United States Patent
Avent et al.

(10) Patent No.: US 10,342,973 B2
(45) Date of Patent: Jul. 9, 2019

(54) THERAPEUTIC ELECTRON AND ION TRANSFER VIA HALF-CELL

(71) Applicant: Kural Corp., Austin, TX (US)

(72) Inventors: Jason Avent, Cedar Creek, TX (US); Shahryar Michael Kiamanesh, Austin, TX (US)

(73) Assignee: KURAL CORP., Austin, TX (US)

( * ) Notice: Subject to any disclaimer, the term of this patent is extended or adjusted under 35 U.S.C. 154(b) by 582 days.

(21) Appl. No.: 14/907,979

(22) PCT Filed: Jul. 29, 2014

(86) PCT No.: PCT/US2014/048742
§ 371 (c)(1),
(2) Date: Jan. 27, 2016

(87) PCT Pub. No.: WO2015/017467
PCT Pub. Date: Feb. 5, 2015

(65) Prior Publication Data
US 2016/0166830 A1      Jun. 16, 2016

Related U.S. Application Data

(60) Provisional application No. 61/859,708, filed on Jul. 29, 2013.

(51) Int. Cl.
*A61N 1/30* (2006.01)
*A61N 1/20* (2006.01)
(Continued)

(52) U.S. Cl.
CPC ........... *A61N 1/303* (2013.01); *A61N 1/0432* (2013.01); *A61N 1/0492* (2013.01); *A61N 1/205* (2013.01);
(Continued)

(58) Field of Classification Search
CPC ........ A61N 1/325; A61N 1/303; A61N 1/306; A61N 1/205; A61N 1/0432; A61N 1/0492; A61M 2037/0007
See application file for complete search history.

(56) References Cited

U.S. PATENT DOCUMENTS 3,530,849 A    9/1970    Watanabe et al.
3,975,170 A    8/1976    Keating
(Continued)

FOREIGN PATENT DOCUMENTS

CA    2530598 C    3/2014
JP    3136797 U    10/2007
(Continued)

OTHER PUBLICATIONS

SM Helfgott, "Unusual digital sparing in rheumatoid arthritis a case of neuropsychoimmunologic involvement", J Clin Rheumatol, Jun. 1997; 3(3):150-2 (abstract).

(Continued)

*Primary Examiner* — Nathan R Price
*Assistant Examiner* — Anh Bui
(74) *Attorney, Agent, or Firm* — Matheson Keys & Kordzik PLLC; Kelly Kordzik

(57) ABSTRACT

A therapeutic electron transfer device including a half-cell and an ionically conductive path for ion transfer between an organism and the half-cell. The half-cell includes an electrically conductive electrode, an active material in contact with the electrode, and an electrically conductive path for electron transfer between the organism and the electrode. The active material includes an oxidizing agent or a reducing agent, such that electron transfer occurs spontaneously from or to the organism, respectively. A kit includes therapeutic electron transfer device and instructions for use. Two therapeutic electron transfer devices may be used simulta- (Continued)

neously or alternately to provide electrons to an organism, withdraw electrons from an organism, or both.

20 Claims, 9 Drawing Sheets

(51) Int. Cl.
    *A61N 1/04*           (2006.01)
    *A61N 1/32*           (2006.01)
    *A61N 1/44*           (2006.01)
    *A61M 37/00*         (2006.01)

(52) U.S. Cl.
    CPC .............. *A61N 1/325* (2013.01); *A61N 1/44* (2013.01); *A61M 2037/0007* (2013.01); *A61M 2207/00* (2013.01); *A61N 1/306* (2013.01)

(56) References Cited

U.S. PATENT DOCUMENTS

| | | | |
|---|---|---|---|
| 4,224,384 A | 9/1980 | Kozawa | |
| 4,856,188 A | 8/1989 | Sibalis | |
| 5,076,287 A | 12/1991 | Johnson | |
| 5,162,042 A | 11/1992 | Gyory et al. | |
| 5,279,543 A | 1/1994 | Glikfeld | |
| 5,443,441 A | 8/1995 | De Claviere | |
| 5,871,460 A | 2/1999 | Phipps et al. | |
| 5,944,685 A * | 8/1999 | Muroki | A61N 1/326 604/20 |
| 7,477,939 B2 | 1/2009 | Sun | |
| 8,386,029 B2 | 2/2013 | Hause | |
| 8,475,689 B2 | 7/2013 | Sun | |
| 2003/0028170 A1 | 2/2003 | Anderson et al. | |
| 2006/0229549 A1 | 10/2006 | Hause et al. | |
| 2007/0286821 A1 | 12/2007 | Phillips | |
| 2010/0003333 A1 | 1/2010 | Watson | |
| 2010/0004521 A1 | 1/2010 | Epps et al. | |
| 2010/0028406 A1 | 2/2010 | Kalia et al. | |
| 2011/0287075 A1 | 11/2011 | Chantalat | |
| 2012/0148633 A1 | 6/2012 | Sun | |
| 2013/0295150 A1 | 11/2013 | Chantalat | |
| 2013/0295184 A1 | 11/2013 | Choi | |
| 2016/0008273 A1* | 1/2016 | Sheftel | A61K 9/0009 424/402 |

FOREIGN PATENT DOCUMENTS

| | | | |
|---|---|---|---|
| JP | 2008226834 | 9/2008 | |
| WO | WO1991016943 A1 | 11/1991 | |
| WO | WO 0113988 A1 * | 3/2001 | ............. A61N 1/205 |
| WO | WO2001013988 A9 | 9/2002 | |
| WO | WO2011130112 A1 | 10/2011 | |
| WO | WO2012006526 A2 | 1/2012 | |
| WO | WO2012012509 A1 | 1/2012 | |
| WO | 2014/153135 A1 | 9/2014 | |

OTHER PUBLICATIONS

N. Daneman et al., "How long should peripherally inserted central catheterization be delayed in the context of recently documented bloodstream infection?", Journal of Vascular and Interventional Radiology, Jan. 2012; 23(1):123-5 (abstract).
Yeunhwa Gu et al., "Drinking Hydrogen Water Ameliorated Cognitive Impairment in Senescence-Accelerate Mice", J Clin Biochem Nutr, May 2010; 46(3): 269-276.
T. Hlaing et al., "Gold Finger:Metal Jewellery as a DiseaseModifying Antirheumatic Therapy!", Hindawi Publishing Corporation, Case Reports in Medicine, vol. 2009, Article ID 518976, Oct. 2009, 2 pp.
Diarmuid M Mulherin et al., "Do gold rings protect against articular erosion in rheumatoid arthritis?", Annals of the Rheumatic Diseases, 1997; 56:497-499.
Arun J. Patil et al., "Biochemical aspects of lead exposure and toxicity in spray painters of Western Maharashtra (India)", Journal of Environmental Health Research, Jan. 2007; 6(2):101-110.
Owen Jarus, "Mysterious Toe Rings Found on Ancient Egyptian Skeletons", LiveScience, Jul. 5, 2013, 4 pp.
"Praxair Technology Enables Processed Juice to Taste Like Fresh Squeezed", Praxair [online], Jun. 22, 2000, retrieved from the Internet: < http://www.praxair.com/news/2000/praxair-technology-enables-processed-juice-to-taste-like-fresh-squeezed>, 3 pp.
Szczupak et al., Living Battery—Biofuel cells operating in in vivo in claims. Energy and Environmental Science 2012, vol. 5, 8891-8895.
International Preliminary Report on Patentability for PCT/US2014/048742 dated Jan. 10, 2015, 6 pages.
Notification of Transmittal of the International Search Report and the Written Opinion of the International Searching Authority for PCT/US2014/048742 dated Dec. 31, 2014, 14 pages.
Atsunori Nakao et al., "Effectiveness of Hydrogen Rich Water on Antioxidant Status of Subjects with Potential Metabolic Syndrome— An Open Label Pilot Study", J. Clin. Biochem. Nutr., Mar. 2010, 46(2):140-149.
Barbara E. Wendland et al., "Lipid peroxidation and plasma antioxidant micronutrients in Crohn disease", Am J Clin Nutr, Aug. 2001; 74(2):259-264.
Ejlarson "Arthritis and bleach", in Pirate4x4.com [online], Nov. 2012, retrieved from the Internet: < http://www.pirate4x4.com/forum/general-chit-chat/1102748-arthritis-bleach.html>, 8 pp.
FG Versteegh et al., "[Magnesium poisoning in an infant].", Ned Tijdschr Geneeskd, Jun. 29, 1991, 135(26):1186-8 (abstract).
J. Kulsh, "Targeting a key enzyme in cell growth: a novel therapy for cancer", Medical Hypotheses, Oct. 1997, 49 (4):297-300.
Joseph Schwartz—Praxair, Inc., U.S. Department of Energy, Hydrogen and Fuel Cells Program: II.D.1 Advanced Hydrogen Transport Membrane for Coal Gasification, FY 2011 Annual Progress Report, 2011, pp. 62-65.
Amarna Project [online], Nov. 2010, retrieved from the internet: <http://www.amarnaproject.com/index.shtml>, 2 pp.
Lower, Galvanic Cells and Electrodes—Biofuel Cells Operating in vivo in Claims. Energy and Environmental Science 2012, vol. 5, 8891-8895.
Examination Report [including machine translation] for Japanese Patent Application No. 2016-531840, dated Jun. 26, 2018, 9 pages.
First Office Action for Chinese Application No. 201480048125.X, dated Jun. 14, 2017, 21 pages.
Intellectual Property Office of Singapore, Search Report and Written Opinion for Application No. 11201600646V, dated Mar. 15, 2017, 9 pages.
Bullen R. A. et al., Biofuel cells and their development. Biosens. Bioelectron., May 15, 2006, vol. 21, No. 11, pp. 2015-2045.
European Search Report for Application No. 14832976.6, dated Jul. 27, 2016, 4 pages.
European Examination Report for Application No. 14832976.6, dated Aug. 22, 2016, 6 pages.
Australian Patent Office; Examination report No. 1 for 2014296315; 5 pages; dated Oct. 17, 2018; AU.

\* cited by examiner

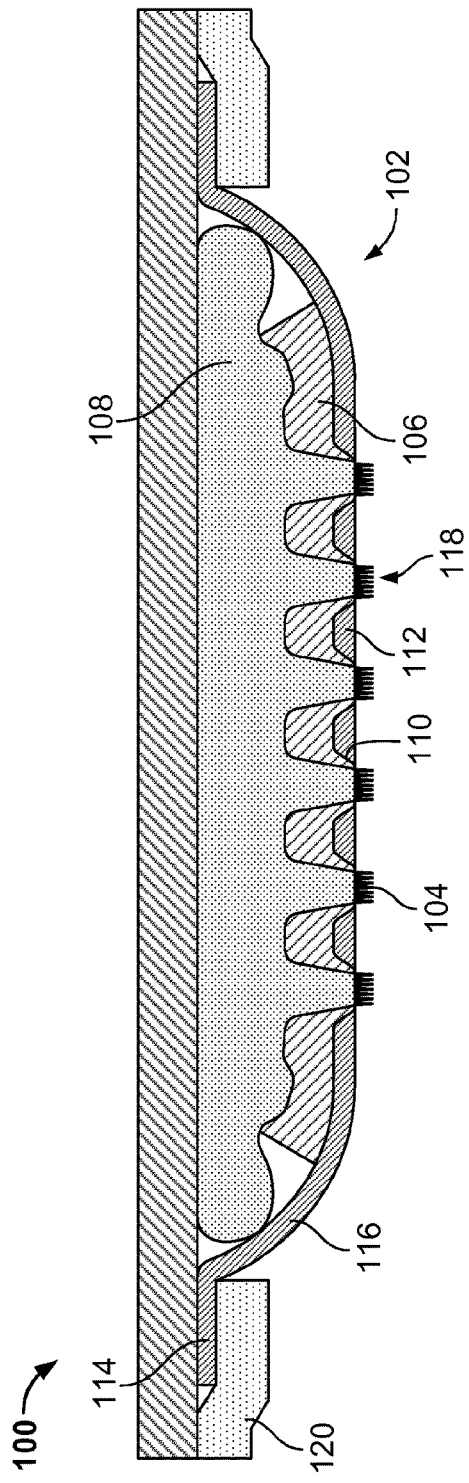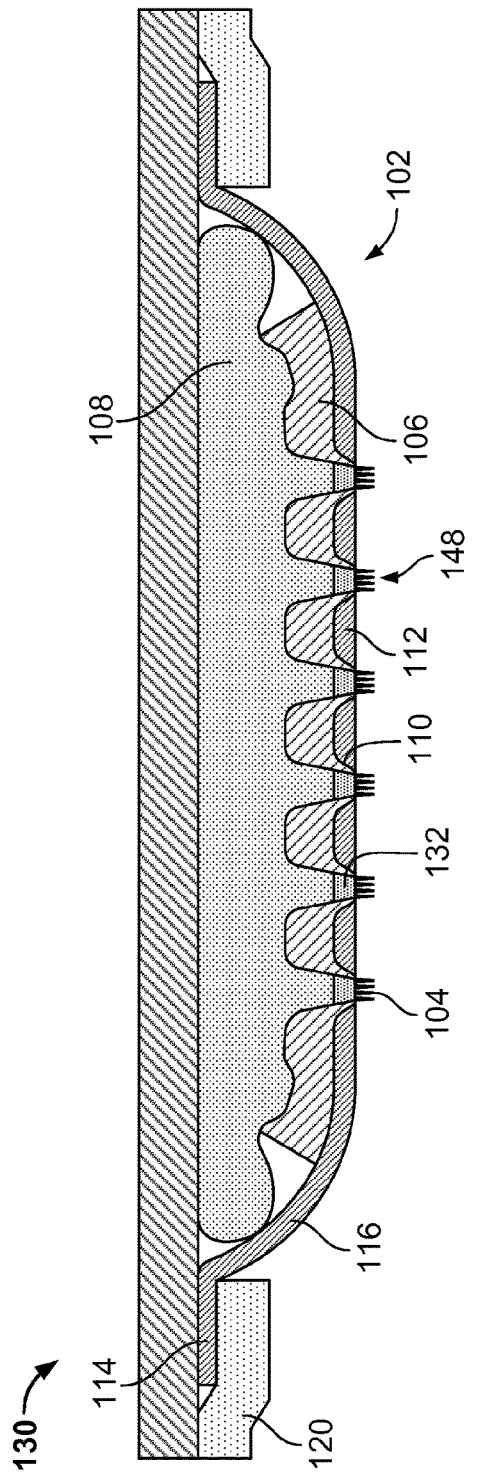

US 10,342,973 B2

THERAPEUTIC ELECTRON AND ION TRANSFER VIA HALF-CELL

CROSS-REFERENCE TO RELATED APPLICATIONS

This application is a U.S. National Phase Application of International Patent Application No. PCT/US2014/048742 filed Jul. 29, 2014, which claims priority to U.S. Application Ser. No. 61/859,708, filed on Jul. 29, 2013, both of which are incorporated herein by reference in their entirety.

TECHNICAL FIELD

This disclosure relates to devices, systems, and methods for therapeutic electron and ion transfer to or from an organism via a half-cell.

BACKGROUND

Antioxidants are widely used as nutritional supplements and believed by some to play a role in the prevention of certain diseases, such as cancer and heart disease. Antioxidant deficiency may cause oxidative stress that is harmful to cells. In contrast, prooxidants are generally believed to be harmful. The presence of prooxidants in the body has been associated with oxidative stress and linked to diseases such as hemochromatosis, Wilson's disease, and human Parkinsonism. Some prooxidants, such as adriamycin, are known to show toxicity toward cancer cells. In organisms, however, antioxidants and prooxidants are generally diffuse, and high levels can be toxic.

SUMMARY

Devices, systems, and methods for therapeutic electron transfer to or from an organism are described. These devices, systems, and methods can be implemented to selectively provide antioxidant or prooxidant effects, thereby increasing or decreasing free radical damage of an organism.

In a first general aspect, a therapeutic device includes a half-cell and one or more ionically conductive paths for ion transfer between the organism and the half-cell. The half-cell includes an electrically conductive electrode, an active material in contact with the electrode, and one or more electrically conductive paths for electron transfer between the organism and the electrode. The active material includes an oxidizing agent or a reducing agent.

Implementations of the first general aspect may include one or more of the following features.

The half-cell may include an electrolyte in contact with the active material. In some cases, the half-cell includes a container configured to contain the electrolyte, the electrode, or both.

When the active material is an oxidizing agent, the therapeutic device, when electrically coupled to an organism via at least one of the one or more electrically conductive paths, withdraws electrons from the organism via the at least one of the one or more electrically conductive paths. Hydrogen peroxide is an example of a suitable oxidizing agent. When the active material is a reducing agent, the therapeutic device, when electrically coupled to an organism via at least one of the one or more electrically conductive paths, provides electrons to the organism via the at least one of the one or more electrically conductive paths. Magnesium is an example of a suitable reducing agent. The therapeutic device is configured to achieve a net transfer of electrons to or from the target.

In some cases, the half-cell includes an additive in contact with the active material. The additive may be selected to increase the rate of electron transfer between the half-cell and the organism. The electrode may include the active material (e.g., in the form of a composite). The electrically conductive path may be formed by the electrode.

The therapeutic device forms a galvanic cell when electrically and ionically coupled to the organism. In some cases, the therapeutic device includes a single half-cell. The therapeutic device may include a support configured to position the therapeutic device proximate the organism or to couple the therapeutic device to the organism, such that electrons are transferred to or withdrawn from a selected location of the organism.

In some cases, at least one of the one or more ionically conductive paths is formed through an opening in an enclosure or container at least partially containing the half-cell. In certain cases, at least one of the one or more ionically conductive paths includes a salt bridge configured to allow ion transfer between the organism and the half-cell.

The therapeutic device may include a battery, such that the battery forms a portion of at least one of the electrically conductive paths between the organism and the electrode, with a first terminal of the battery coupled to the electrode and a second terminal of the battery coupled to the organism.

In some implementations, the therapeutic device includes an enclosure having a surface configured to contact the organism, and the one or more ionically conductive paths are formed through the surface of the enclosure configured to contact the organism. In some cases, the flow rate of ions through the one or more ionically conductive paths at the surface of the enclosure is inversely related to the ratio of the total area of the one or more ionically conductive paths at the surface of the enclosure to the sum of the total area of the surface configured to contact the organism and the total area of the one or more ionically conductive paths at the surface of the enclosure.

The therapeutic device may include a drug or nutritional supplement proximate at least one of the one or more ionically conductive paths, wherein therapeutic device is configured to deliver the drug or nutritional supplement to the organism via the at least one of the one or more ionically conductive paths.

In a second general aspect, a kit includes a therapeutic electron transfer device configured to achieve a net transfer of electrons to or from an organism when coupled electrically and ionically to the organism, and instructions for coupling the therapeutic device to an organism.

Implementations of the second general aspect may include one or more of the following features.

In some cases, the kit includes instructions for replacing or maintaining the therapeutic device. The kit may include an electrolyte for the therapeutic device. The kit may also include instructions for preparing electrolyte for use in the therapeutic device, delivering the electrolyte to the therapeutic electron transfer device, or both. In certain cases, the therapeutic electron transfer device includes the therapeutic device of the first general aspect.

In a third general aspect, a therapeutic device is fabricated by contacting an electrically conductive electrode and an active material including an oxidizing agent or a reducing agent, contacting an electrolyte with the active material, providing an electrically conductive path configured to allow electron transfer between the electrically conductive electrode and an organism, and providing an ionically conductive path configured to allow ion transfer between the active material and the organism.

In a fourth general aspect, treating an organism includes electrically coupling an anode half-cell to the organism, electrically coupling a cathode half-cell to the organism, and alternately activating the anode half-cell and the cathode half-cell to effect a non-simultaneous transfer of electrons to and from the organism, respectively.

In a fifth general aspect, treating an organism includes transferring electrons and ions to the organism by electrically and ionically coupling a therapeutic device comprising a half-cell to a surface of the organism, wherein the therapeutic device comprises one or more ionically conductive paths, and the rate and velocity of ion transfer to the organism via the one or more ionically conductive paths is inversely related to the ratio of the total area of the one or more ionically conductive paths at the surface of the organism to the total area of the therapeutic device at the surface of the organism.

Implementations of the fifth general aspect may include one or more of the following features.

In some cases, the therapeutic device includes a drug or nutritional supplement, and treating the organism includes transferring the drug or nutritional supplement to the organism via the one or more ionically conductive paths. The therapeutic device may place or include an ionomer with a single charge (+ or −) immobilized in a solid or gelled matrix impeding the flow of same charged ions and allowing flow of only one type of ion (− or + respectively).

In any of the above aspects or implementations, the organism may be a human.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

BRIEF DESCRIPTION OF THE DRAWINGS

FIGS. 1A and 1B are cross-sectional views of embodiments of a therapeutic electron transfer device in the form of an adhesive patch.

DETAILED DESCRIPTION

Figure 1C:
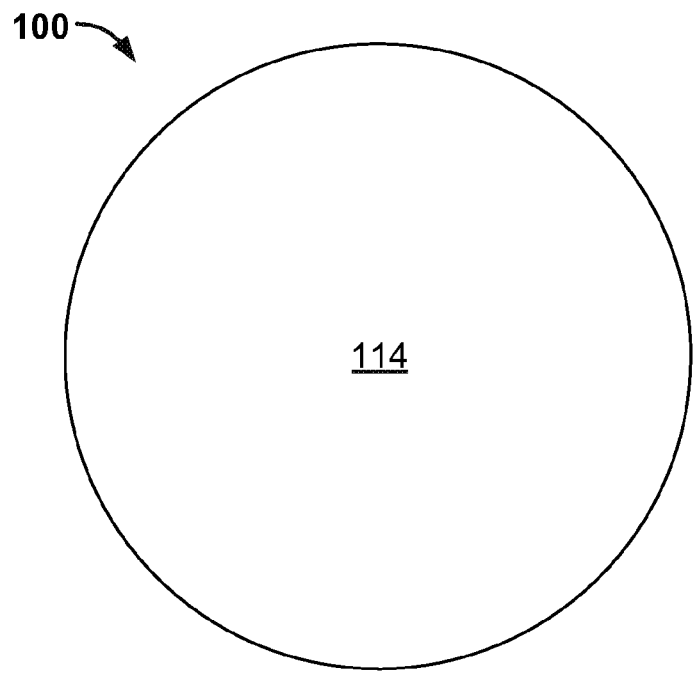
FIGS. 1C and 1D are top and bottom views of the therapeutic electron transfer device of FIG. 1A.

This disclosure relates to devices, systems, and methods for therapeutic electron and ion transfer to or from a target via a half-cell. The electron transfer may be achieved via a galvanic half-cell electrically and ionically coupled to the target or via a power source electrically coupled to the target. The target is typically an organism. Organisms include, for example, humans, mammals (e.g., livestock and pets), insects, plants, fungi, and microbes. Electron transfer to or from an organism via a half-cell coupled to the organism may occur in-vivo or post-mortem. An object, including a surface, may be electrically coupled to a half-cell to achieve a desired effect on organisms in contact with the object, such as sterilization or pest control. Media, such as bioreactor media, microbiological media, fermentation media, horticulture media, fungiculture media, and reservoirs (e.g., water supplies, aquatic gardens, swimming pools, hot tubs) may be electrically coupled to a half-cell to promote or retard growth of organisms in the media.

Electron transfer to and from a target is achieved by electrically coupling a half-cell or a power source to the target. The half-cell includes an electrically conductive electrode, an active material, and includes or is configured for use with an electrolyte. That is, as used herein, a half-cell may be a "wet" half-cell, including an electrolyte, or a "dry" half-cell, to which an electrolyte is added or brought in contact with for operation. As used herein, "electrolyte" generally refers to a substance that ionizes when dissolved in a suitable ionizing solvent, such as water, or an electrolyte solution formed when a substance that ionizes is placed into a suitable ionizing solvent. Suitable ionizable substances include chloride salts such as sodium chloride and potassium chloride, sulfate salts, nitrate salts, and ionomers. Generally, any salt that increases the solubility of electrode corrosion products when the salt's ions are exchanged with corrosion products are suitable as electrolyte salts. Corrosion products include any of the salts of ions that are produced by the reduction or oxidation of the active material in the half cell. During operation, the electrode is in contact with the target or an electrically conductive medium that is in contact with the target. In one example, the target is an aquatic organism, and the electrode is in contact with seawater in which the aquatic organism is contained.

The electrode is an electrical conductor that provides an electrically conductive path between the half-cell and the target, thereby allowing the transfer of electrons from the half-cell to the target or vice versa. The active material and the electrical conductor may be the same or different. In some cases, the active material and the electrical conductor are in the form of a composite. When the active material is a reducing agent, the electrode functions as an anode. Suitable reducing agents include metals, organic compounds, and combinations thereof. Suitable metals include lead, aluminum, copper, zinc, beryllium, magnesium, sodium, calcium, strontium, barium, potassium, and lithium. When the active material is an oxidizing agent, the electrode functions as a cathode. Suitable oxidizing agents include but are not limited to hydrogen peroxide, potassium permanganate, lead oxide, sodium percarbonate and potassium peroxymonosulfate.

In some cases, the half-cell includes a container to contain the electrolyte. The container may be open, sealed, or water-tight, and may be of any size or shape. Some containers are rigid and unexpandable, and others are flexible and expandable. In some cases, the active material defines openings that function as a container to contain the electrolyte. In certain cases, a fluid from the target contacts the half-cell during use and functions as the electrolyte. This fluid can be in contact with an ionomeric substance to complete the ionically conductive path between the target and the active material of the half-cell.

The half-cell is electrically coupled to the target directly or indirectly via the electrode, thereby forming an electrically conductive path between the target and the electrode. In one example, a body fluid of a target in contact with the electrode of a half-cell serves as the electrolyte and also functions as an electrically conductive material to transfer electrons between the electrode and the target.

An ionically conductive path allows a flow of ions between the half-cell and the target. The ionically conductive path is salt bridge. In some cases, "salt bridge" refers to a device used to ionically couple oxidation and reduction half-cells (or cathode and anode half-cells, respectively) of a galvanic cell. In certain cases, the ionically conductive path is formed by the electrolyte or other fluid, and a separate explicitly engineered device is not required. In certain cases, the electrically conductive path and the ionically conductive path are the same material or may be a composite of an ionic conductor and an electrical conductor (e.g., a mixed conductor). Salt bridges are typically constructed to limit electrical flow and maximize ion flow. These are sometimes made of a gelled or solid material to allow specific ions to flow between the half-cells. In the past, the salt bridge was used to separate incompatible chemistries in batteries and was engineered to not be a bottleneck in the flow of electricity from a battery. Salt bridges have been composed usually of ceramic or a gel contained within a support that prevents drying of the material within the salt bridge. Most modern batteries operate in a common electrolyte or have the salt bridge reduced to a membrane within the device. A salt bridge can be accomplished by a continuous path of water or bodily fluid that contacts the organism.

Increasing or decreasing the cross sectional area of the ionically conductive path or the salt bridge can lead to different effects depending upon the depth of penetration and the quantity of ions that flow into the target. Selecting the site of ionic coupling to the organism and extending the ionically conductive path away from the active material can allow specific ions, buffers, or chemistries to be loaded into the electrolyte at the end of the salt bridge that contacts the target.

When a half-cell or one terminal of a power source is electrically coupled to a target, the half-cell or the power source functions as a first half-cell and the target functions as a second half-cell of a galvanic cell. In one example, when an anode half-cell with an anode (an "anode half-cell") is electrically coupled to a target, the target functions as a half-cell with a cathode (a "cathode half-cell) and receives electrons from the anode half-cell ("anodic effect"). In another example, when a cathode half-cell is electrically coupled to a target, the target functions as an anode half-cell and provides electrons to the cathode half-cell ("cathodic effect"). By selectively coupling a target to a power source, the power source may function as either an anode half-cell or a cathode half-cell. As used herein, "anode half-cell" generally includes a power source coupled to a target in such a way as to function as an anode half-cell by providing electrons to the target, and "cathode half-cell" generally includes a power source coupled to a target in such a way as to function as a cathode half-cell by withdrawing electrons from the target.

Electrons are spontaneously transferred to a target via an anode half-cell electrically coupled to the target. The anode half-cell includes an electrical conductor and one or more reducing agents as an active material. Examples of reducing agents include metals, organic compounds, and other elements or substances that have a greater reduction potential (more negative) than the electrochemical potential of the target. Electrically coupling an anode half-cell to an organism supplements the organism's supply of electrons and serves a beneficial, antioxidant function. In some cases, an anode half-cell functions as a sacrificial anode.

Electrons are spontaneously transferred from a target via a cathode half-cell electrically coupled to the target. The cathode half-cell includes an electrical conductor and an active material including one or more oxidizing agents. Examples of oxidizing agents include compounds that have a reduction potential that is lower (less negative) than the electrochemical potential of the target. In contrast to the electron supplementation provided by electrically coupling an anode half-cell to an organism, electrically coupling a cathode half-cell to an organism may have deleterious effects on the portion of the organism proximate the region to which the cathode half-cell is electrically coupled. In one example, transferring electrons from an organism promotes free radical chain reactions in a specific region of the organism, thereby serving a prooxidant function. In another example, transferring electrons from a specific region of an organism promotes oxidation of a therapeutic substance provided to that region of the organism. In yet another example, transferring electrons from a surface electrically coupled to a cathode half-cell promotes surface sterilization by withdrawing electrons from microbes on the surface.

As used herein, a "therapeutic electron transfer device" or "therapeutic device" includes an electron source or sink, an electrically conductive path between the electron source or sink and the target, and an ionically conductive path configured to allow a flow of ions between the target and an electrolyte. In some cases, a therapeutic electron transfer device or therapeutic device includes a structure configured to position a half-cell or an electrode proximate a particular region of an organism (e.g., the head, arm, leg, or torso of a human) or to direct electron flow to the organism from the half-cell to the organism or from the organism to the half-cell. Use of a therapeutic device or therapeutic electron transfer device results in a net transfer of electrons.

In some cases, a therapeutic electron transfer device includes a single electron sources or a single electron sink (e.g., a single anode half-cell or a single cathode half-cell). In some cases, two or more half-cells are electrically coupled to a target for simultaneous or alternating use. In one example, two anode half-cells or two cathode half-cells are coupled to a target and used simultaneously to increase the delivery or removal rate of electrons or to treat different areas of a target. In another example, an anode half-cell and a cathode half-cell are applied to different areas of a target and are used alternately (e.g., out of phase) to achieve a desired effect. As described herein, an anode half-cell and a cathode half-cell are not activated simultaneously with respect to a common target.

A half-cell may be designed for ingestion by a target, implantation in a target, contact with a target, or a combination thereof. A half-cell for ingestion may include active material coated with a substance to delay release in a target. In one example, an ingestible half-cell is coated in wax or oil for selective activation in the digestive tract. In some cases, greater electron transfer from a half-cell to a target may be achieved via implantation of a half-cell in the target than by surface contact of a half-cell with the target. Fluids in an organism may serve the role of electrolyte for an implanted or in vivo half-cell. In some cases, implantation and surface contact may be combined for an additive effect.

In some cases, a half-cell includes an electrode in contact with an electrolyte, one or both of which may contact the target directly. In other cases, a half-cell includes a container that contains the electrode and inhibits direct contact of the target and active material, the target and the electrolyte, or both. The container may be sealed. In some cases, the container is ion- and water-tight, and is fluidically coupled to an ionically conductive path to allow a transfer of ions between the half-cell and the target. Some or all of the container may be electrically insulating, such that electron transfer to or from the target occurs via a selected electrically conductive path between the target and the electrode rather than via the container itself. Likewise, the container may be ionically non-conductive and define an opening to deliver ions to the target.

In one example, a half-cell is in the form of an electrode sealed in a container (e.g., an enclosure) configured to be electrically and ionically coupled to a target. The enclosure may be in the form of an adhesive patch. Electrical coupling between the half-cell and the target may be increased by cleansing the intended area of the target, removal of insulating substances (e.g., hair, dead skin, etc.) from the surface of the target in the area intended for the half-cell, application of a conductive substance such as electrolyte or electrolytic gel to the intended area of the target, or a combination thereof. The electrolyte typically contains some component of water and some dissolved salts to provide a larger ionically conductive area in contact with the organism. Commercially available EEG gels and pastes are commonly used for this purpose. In some cases, surface contact is achieved by forming at least a portion of a half-cell into wearable device, such as a bracelet.

As described herein, an electrode is typically an electrically conductive solid that is coupled to (e.g., electrically, physically, or both) or in contact with the active material. The electrode may be selected to hold the weight of a solid active material coating without substantial deformation. When the active material is a fluid, the electrode may have a catalytic surface and enough surface area to promote the desired electron flow. Channels or pores in the electrode or active material may enhance electron flow to or from the half-cell. The electrode may be in the form of a scaffold, mesh, fabric, rod, or wire. The scaffold may be regular or irregular. The wire may be in any configuration. In some cases, the electrode is in the form of fused particles or a regular or irregular solid.

For an anode half-cell, the reducing agent is selected to have a more negative reducing potential than the target organism. Magnesium is an exemplary reducing agent. Magnesium is compact, light, inexpensive, nutritionally beneficial, and energy dense compared to other biological reducing agents, is one candidate for human use due to its low toxicity and ease of use.

A power source may also be used to drive a flow of electrons to a target. In stationary applications in which the power source is continually available, a constant source of electrons can be provided with minimal maintenance and no chemical handling. A power supply may be implemented by coupling one lead to an electrolyte that is coupled to a target via an ionically conductive path, while the lead from the opposite terminal is coupled directly or indirectly to the target. In one example, to donate electrons with a power supply, the positive terminal of the power supply is coupled to an electrode in contact with an electrolyte solution that is coupled to a target via an ionically conductive path. The negative terminal is electrically coupled directly or indirectly to the target to allow electrons to transfer into the target.

As described herein, a cathode half-cell includes an electrical conductor and an oxidizing agent. The oxidizing agent may be in the form of a solid, liquid, or gas. One example of a suitable oxidizing agent is hydrogen peroxide. Corrosive conditions typically occur within a cathode half-cell; corrosion of the electrical conductor may be mitigated by using an electrical conductor that includes platinum or carbon fibers. For delivery of cathodic effects to large parts of a target, conductive plastic impervious to the oxidizing agent may be used to shield a user from skin damage while allowing the electron withdrawal to be evenly distributed and avoiding toxicity caused by direct skin contact with the oxidizer. Other suitable oxidizing agents include potassium permanganate and solid forms of hydrogen peroxide bound to another salt. Examples include sodium percarbonate and potassium peroxymonosulfate. A power supply may be used to withdraw electrons from a target, or may be used to make an oxidizing agent in situ.

In some cases, reaction products may be removed from a half-cell via reactants in the electrolyte, or an electrolyte may be replenished to accelerate electron transfer. Removing saturated or depleted electrolyte may help keep an electrode surface cleared of reaction products and thereby allow the surface to continue reacting. In one example, replenishment of sodium chloride in an electrolyte solution along with the removal of products such as sodium hydroxide and magnesium chloride allows the system to once again function in a manner similar to its activity when first activated and may shift the equilibrium toward the production of magnesium chloride and sodium hydroxide from the reactants $Mg(OH)_2$ and NaCl. A half-cell container may include one or more ports for providing an electrolyte to a half-cell, for removing an electrolyte from the half-cell, or both.

An additive may be included with or provided to a half-cell to improve performance (e.g., electron flow, ion flow or consistency over the lifetime of electrode use) of the half-cell. Additives include, for example, catalysts, reactants, absorbents, and adsorbents. Manganese dioxide ($MnO_2$) may be included in a half-cell that produces hydrogen to consume hydrogen gas and inhibit the buildup of pressure in the half-cell. The manganese dioxide may be used in sealed half-cells, or may be recharged by exposure to oxygen. In this way, the manganese dioxide serves a depolarizing function by reserving enough oxygen to react with the hydrogen generated in a half-cell.

In certain cases, products formed in a half-cell may interfere with its function. Gases such as hydrogen can lead to a loss of electron flow from the half-cell, and having materials like manganese dioxide that absorb this hydrogen may enhance performance. Likewise, noxious or fouling compounds like hydrogen sulfide may be absorbed from a half-cell by an absorbent material proximate the half-cell. Substances like activated carbon may be included in a half-cell to adsorb gases such as hydrogen sulfide.

Biological organisms or enzymes may also be included in a half-cell. In one example, biological organisms that produce acids may be used to maintain the activity of an electrode.

In a cathode half-cell with hydrogen peroxide as the active material, manganese dioxide can be used to catalyze the conversion of hydrogen peroxide to oxygen and may promote activity of the cathode. Waiting until it is time to activate the cathode and then putting a manganese dioxide-doped electrode into the hydrogen peroxide may promote ease of use, transport, and deactivation when the catalyst-treated surface is removed from the hydrogen peroxide. Manganese dioxide is just one example of a reactant or catalyst that may be added to improve the quality, quantity, or products of a half-cell reaction. In another example, silver may be used to enhance the ability of manganese dioxide to consume hydrogen gas from an anode half-cell with magnesium.

When casting magnesium or other solid substances for use as the active material with half-cells, a dissolvable component may be included with the magnesium or other solid substance. This slowly dissolving component like a salt, for instance, may be combined with the magnesium or solid substance cast in a mold. During operation of the half-cell, dissolution of the component may lead to voids that can be shaped as determined by the placement of the component during casting. The amount of solvent-tunneled surface area may be tailored to the desired activity level of the electrode.

Solvation of salts provides the additional benefit of supplying an ion exchange salt dissolved into the electrolyte adjacent to the surface of the anode at a high concentration. The dissolving salts increase electrolyte density, thereby promoting a convection of fluid downward across the face of the electrode. As these salty solutions fall, they contact the electrode's surface, which may be corroded. Soluble ions like potassium and chloride exchange ions with insoluble surface metal oxides. In this example, magnesium hydroxide combines with salt ions to make soluble salts as products via ion exchange. In this example, potassium chloride is used to create two soluble products, magnesium chloride and potassium hydroxide, thereby removing the outer layer of oxidation products. Soluble counterions in the salt that dissolves from within the surface of the magnesium maintains electrode activity by stripping oxidation products such as insoluble magnesium hydroxide ($Mg(OH)_2$). These salt inclusions may also help rectify the deficiencies and impurities of the water used for electrode activation. This salt inclusion means that water instead of an electrolyte can be used to wet the half-cell. When tap water is used for a half-cell and could be of questionable quality, salts that dissolve slowly in the half-cell provide an electrolyte as well as a defense against passivating compounds such as iron that may be present in tap water. Even as the anode does become passivated, solvation does not depend upon electrode activity to continue apace. That is, the self-uncovering nature of the introduced salts or other dissolvable substance may reactivate the electrode by exposing fresh surfaces.

One or more additives may be combined with an active material (e.g., as an active material is cast). These additives may be selected to enhance the structural or catalytic function of the half-cell, to change the structural integrity of the half-cell, to change the response of the half-cell to environmental conditions, or a combination thereof. Hygroscopic materials such as clay or salts can be disposed among magnesium as it is cast or as a surface coating on the mold. In one example, clay is used as a surface disruptor by expanding in the presence of water, thereby exposing new surfaces for reaction. Other hygroscopic materials that expand such as salts may also demonstrate a similar "revealing effect" that exposes new active material surfaces to attack by water once wetted. Like dissolution of salts in active materials, the use of a hygroscopic salt mixed with the active material can be used to convert water into an electrolyte. Clay that is wetted with potassium chloride solution, vacuum pulsed and then dried would combine the beneficial activation features of both the dissolvable potassium chloride and the expanding, but insoluble clay. Carbon can also be included to weaken the structure of the anode while it also provides an electrical path out of the anodic substance.

Inclusions within an electrode can also have an expansion and contraction cycling with thermal expansion. A substance with a greater thermal expansion coefficient may allow cycles of heating and cooling to shrink and expand the surface of an active material, allowing a refreshing of the surface, even when the surface is passivated. This expansion may be due to freeze-melt cycles, and some materials like gallium, silicon, germanium, bismuth, and water share the ability to expand upon freezing to the solid form. Other additives that shrink while solidifying may also be used to disrupt the surface of an active material. If this freezing/melting/boiling point is passed during the usual service cycles of the half-cell then the substance may be useful in destabilizing the surface of the active material. Liquids can run out of pores or channels formed by the disruption, and gasses can be released from solids via sublimation or from liquids by boiling.

In some cases, bubbles of gas can be used to honeycomb the structure of an active material during formation or casting. Gasses such as carbon dioxide may be useful to include as a reactant within the structure. Similarly, a liquid may be introduced into the casting process such that it leaves a liquid channel within the active material that can be later drained away. Materials such as gallium may be used to create liquid-filled tubes within a hot cast anodic substance, that when ruptured and drained leaves a hollow tube defining a void that functions as a container for an electrolyte. In this way, a metal such as magnesium may be cast around a conductive material (e.g., a conductive scaffold), but retain some liquid filled internal space that is later filled with electrolyte.

Physical disruption of an active material structure internally allows factors like temperature, moisture, dissolution, absorption, expansion, and contraction to work upon the active material surface, such that the active material may be revived and renewed. In this way, the admixture of physically disrupting, non-electrochemical features in the solid structure of the active material itself is applicable to half-cell design for protection of metallic equipment in passivating waters that would, for instance cause a passive coating of iron to form on the active material surface from the soluble iron sulfide.

Another method to promote physical disruption of an active material is one that incorporates regular mechanical disruption of the surface. This may be accomplished by making the anode in a way that it is abraded, such as scraping the oxide coating and exposing bare metal. Abrasion may also be incorporated into the operation of a half-cell, as described herein with respect to a chewable anode half-cell for which chewing allows the cycling of active material that breaks up the active material to expose new, reactive surfaces.

A non-corroding electrically conductive material may be included with an active material. An active material may be cast and then coupled to a conductive wire to help direct electrons out of the half-cell and to a target. In some cases, the active material may be formed with admixed conductive fiber, thereby promoting activity of the active material while providing a strengthening reinforcement for the active material.

In some cases, an electrode is positioned within the active material as an admixture at the time of casting, or as an additive to the mold surface before casting. The use of carbon fiber or carbon black admixed with molten magnesium may reduce the incidence of insulating magnesium hydroxide at the surface of the active material. If whiskers of carbon fiber protrude out of the surface and are shed and renewed because they are embedded throughout the active material, then the problem of a resistive coating is reduced. An electrode may also be placed within an active material's structure that is not subject to the electrically resistive coating of oxidized products of the half-cell. Carbon fiber, which is relatively inert and non-toxic, may be incorporated within an active material to yield a composite electrically conductive material. In one example, the composite electrically conductive material is in the form of a scaffold. The linearity of short overlapping strands may improve both the electrical conductivity/gram loaded compared to activated carbon, and may increase the strength and physical properties of the active material.

A degradable internal conductive material may offer time-release properties suitable for ingestible half-cells. Active materials may be cast with reactants and catalysts together, and with physical structures constructed of carbon. Internal channels and macrostructures for injection of materials post-casting will allow temperature sensitive components and electrolyte salts, nutrients, and the like, to be added to the ingestible half-cell. It is also possible to cast magnesium powder along with other powdered ingredients to make a powder-based product that is pressed with high pressure and or speed to become sintered.

A degradable coating may be used to coat a half-cell to achieve appropriate release at the target site. The coating may be, for example, a polymer or oil. In one example, an ingestible half-cell coated with oil may be activated by bile as the half-cell enters the small intestine. The emulsifying action of the bile strips the oil coating to provide an active surface, but only after the half-cell has passed through the acidic environment of the stomach.

In some cases, a half-cell includes a water-tight container. All or a portion of the container may be electrically insulating. In one example, the container is plastic. Containers may be especially suitable for use in power source implementations in which charge needs to be directed to a specific location to be effective. In some implementations, the active material is in direct contact with the target or the target's environment (e.g., a saltwater pool in which the target is located). In one example, when the target is a digestive tract, a container may be implemented if delayed release is required, but otherwise not implemented.

A container may allow increased volume and freer flow of electrolyte when the half-cell is used in an otherwise dry environment. An electrically insulating container may inhibit the generated electrical potential from straying to an unintended target or unintended portion of the target. This container may also contain catalysts and products in the half-cell. In some cases, the container is a vented enclosure that allows gasses such as hydrogen to escape. In certain cases, the physical expansion of reaction products such as $Mg(OH)_2$ can be accommodated by an accordion-like, sleeve and piston, or other structure that accommodates expansion physically.

Venting is suitable for electrodes that produce gases not otherwise sequestered or reacted. Adding a sufficient amount of $MnO_2$ to a half-cell, for instance may eliminate a need for venting. There may also be a desire to ventilate a half-cell actively. If a less than sufficient amount of $MnO_2$ were included within a half-cell, drying out of the electrode would allow atmospheric oxygen to regenerate $MnO_2$ from MnO (OH) created by the reaction with hydrogen. This may reduce the cost and bulk of the electrode. In some cases, a semi-permeable film or active agitation of a half-cell is implemented to force air in and out of the half-cell, even while in use. This agitation may be achieved via actions such as breathing, walking, or an active pumping action by a target or a provider.

For cathode half-cells, atmospheric oxygen may be suitable as the active material with an appropriate catalyst. In some cases, an exchange of air may be adequate to keep the cathode active. Venting is beneficial for cathode half-cells that include hydrogen peroxide as the active material, since reduction of hydrogen peroxide yields gaseous oxygen.

An electrically conductive path is established between the half-cell and the target to which it is electrically coupled. For a half-cell with a container, the electrically conductive path electrically couples the electrode and the target. This electrically conductive path may include an electrically conductive material in addition to the electrode. This electrically conductive material may be a solid material such as a wire, a conductive liquid or gel, or a conductive fabric that allows charge to flow from the half-cell to the target. Some half-cells may be implanted or attached directly to a pre-existing post (e.g., a piercing post) and may not require a separate or extensive conductive path. In some cases, a wire is suitable to transfer electrons to or from a half-cell via a non-corroding surface of the half-cell. Electron flow to or from the half-cell may reduce or inhibit corrosion along an electrically conductive path.

In some cases, transfer of electrons is achieved via an electrically conductive path (e.g., a wire) inserted or implanted with body fluid providing serving as the electrolyte. In some cases, an electrically conductive path may be ten feet or more in length. For a cathode half-cell, more selective placement of a shorter electrically conductive path may be suitable. That is, since the cathodic effect may be deleterious to a target, more precise direction is appropriate. Generally, when a half-cell is used to treat a specific region of a target, a shorter electrically conductive path may be advantageous.

The electrically conductive path can terminate at the target's surface, or an electrode can be implanted to increase flow to a particular region of the target. When the target is an organism, implantation includes insertion into a body cavity such as the mouth, digestive system, reproductive, sinus, outer ear, inner ear, urinary tract, bladder, etc. A path can be made surgically as well to implant the electrically conductive path or the half-cell directly within an incision. The electrically conductive path may further be shielded by a non-electrically conducting material so that only a portion of the electrically conductive path is in contact with the target.

In some cases, the electrically conductive path to the half-cell is via an external surface of a target. This connection may be enhanced by an electrolyte such as an electrolytic gel. When the target is a human or other mammal, the process of electron transfer at the skin surface can be enhanced by cleaning, shaving, or otherwise removing non-electrically conductive materials before the connection is made. At this interface, the electrically conductive path may be designed to maximize surface area and skin contact so that electron transfer does not bottleneck at the interface between the skin and the half-cell's electrically conductive path.

An electrically conductive path to a human or mammal target may be enhanced by the natural electrolyte properties of bodily fluids and secretions. Some half-cells work when immersed in body fluids as electrolytes. In one example, an electrically conductive path or a half-cell is inserted into an orifice or a target. In another example, a half-cell is coupled to an intravenous needle during medical care. The needle reaches directly into the blood stream, which provides an electrical path throughout the body that is free of cell membranes that create a higher resistance through general tissues.

In some cases, an anode half-cell and a cathode half-cell are activated alternately with respect to intravenous treatment. The anode half-cell may facilitate needle self-cleaning and prevention of bacterial fouling of the needle or catheter by anaerobic organisms. A cathodic treatment of an intravenous needle may serve to kill adhering bacteria. Alternation of these two effects may be implemented to destroy unwanted microbes. This may be especially important when centrally implanted lines such as PICC (Peripherally Inserted Central Catheter) lines are used. These cannot currently be placed in a patient with current septicemia because of concerns about bacterial seeding on the line.

Bacterial fouling may be mitigated by alternating the use of anode and cathode half-cells. This alternation of anode half-cell, then cathode half-cell separated in time and often in space may be referred to as "alternating anode and cathode pasteurization" (AACP). This method may be suitable for sterilizing implanted items. If the anode half-cell and cathode half-cell are swapped by a three-way relay, a change in voltage occurs along the electrically conductive path and through the fluid within the catheter. This reversal from anodic to cathodic charge potential will de-aggregate ionic and covalent contact with the medical device, leading to a "cleansing" of surfaces and a breakup of biofilms. Microbes unable to tolerate such a fundamental shift in environment may perish as potentials change quickly. This alternation may be combined with ultrasound or infrasound vibration on the catheter to dislodge organisms during the treatment.

When alternation of cathode and anode half-cells is applied to electrically conductive surfaces or bodies of water (e.g., floors, countertops, saltwater pools), a similar sterilization process occurs. Treatment may be automated to avoid cathode activity when the user is present, for example, by having the user's presence trigger anode activity. Implementation may include use of a power source and a controller capable of alternating cathodic and anodic functions.

Design considerations described herein provide guidance for building half-cells suitable for a variety of applications. At each consideration of the optimized design, a different option may be chosen depending upon intended use. Once the design has been selected and implemented, maintenance tasks and instructions for use facilitate the desired outcomes.

Beyond design, there is a level of user instructions and maintenance tasks that promote efficient functioning of a half-cell. In some cases, replacement, replenishment, or refreshment of an electrolyte may promote efficient functioning of a half-cell. If an active material is in excess stoichiometrically compared to the volume of electrolyte, then the electrolyte may need to be emptied and refreshed. If the active material is in the form of a ring, for instance, a hollow tube of silver may be integrated into the structure. The tube may have two ports on the surface of the ring, one for the entrance of new electrolyte, and the other for exit. In some cases, the roles of these ports may be interchangeable, or there may be a one-way flow. A syringe may be used to provide new electrolyte solution or water through and flush the saturated electrolyte through. A port might, for instance, be hidden beneath a stone in a ring, or it may include two openings facing the interior of the ring. The ports may remain open or may be plugged between use to inhibit leakage and loss of activity.

In some cases, as described herein, some active materials may include the salts for the electrolyte needed for the full quantity of active material to degrade. If a half-cell is to be drained and refilled with electrolyte, then a charge of low solubility salt within the spaces of the active material may allow multiple rounds of fresh water injection before all salts have dissolved.

In other cases, some active materials do not include salts for electrolyte function. An electrolyte may be obtained ready for use or prepared by dissolution of salts in water for recharging the electrolyte. A container holding a half-cell may be flushed before replenishment of the electrolyte. Starting with purified water may help promote consistent results. However, saliva is an acceptable electrolyte and has the advantage of being readily available. For half-cells with a liquid active material such as hydrogen peroxide, the electrolyte contains the active material, and replenishing the electrolyte includes introducing additional active material as well. In the example of a hydrogen peroxide active material, electrolyte salts may be admixed with the hydrogen peroxide solution to achieve the desired electrical conductivity.

Half-cells may be monitored for depletion of active material. Spent active material may be replaced with a new quantity of active material, or the entire half-cell may be replaced. Visual and other signs of active material depletion may be monitored. In the example of magnesium, the appearance of a conductive support may indicate depletion of magnesium coated on the support. A hydrogen sulfide odor may be detected if a bare magnesium anode is active. This "sniff test" has the advantage of also detecting electrode passivation. In addition, the appearance of an active material surface may change when passivated. For magnesium, a change in color from the usual silvery white or gray may indicate that the anode has been passivated.

Half-cells may be tested for the voltage they produce via a voltmeter or other indicator such as an LED light or amplifier that detects the electrical activity of the half-cell. In a half-cell that is designed to produce hydrogen, hydrogen production may be visually assessed in an acidic solution by the appearance of hydrogen bubbles. These can be collected and to give an indication of anode activity level by the quantity of hydrogen produced per unit of time.

For a half-cell containing hydrogen peroxide, one test is to take a sample of the hydrogen peroxide solution and expose it to manganese dioxide. The manganese catalyzes the formation of oxygen and water from hydrogen peroxide. This shows as small oxygen bubbles when hydrogen peroxide solutions are put onto a surface treated with manganese dioxide.

A passivating surface may be removed from a catalyst or active material in a half-cell. Loss of function may be caused by a deposit of passivating substances on the surface of a catalyst or on the surface of the active material. Sometimes, this will be a buildup of material like magnesium hydroxide which forms a protective coating across the active material. Other times, it may be due to contamination of the active material by impurities in the electrolyte or the environment. If magnesium is no longer active, a solution of citric acid may be used to strip away buildup from the magnesium and leave a bright white, active surface. Other methods of cleaning an active material include mechanical vibration (e.g., ultrasound cleaning), vigorous flow of electrolyte solution, or exposure to an active material such as hydrogen to solubilize fouling accumulations.

For anode half-cells, there is little harm in directing the charge to an area outside the intended region of the target. Symmetrical results may be promoted by implementing a pair of anode half-cells symmetrically, or regularly switching the point of contact of a single anode half-cell. A single centrally located anode in a wearable configuration (e.g., in a necklace or a ring on each hand) may be advantageous.

Ports from the device to the user may be patterned to conform to the shape and depth of tissue to be treated with ions. If the ions flowing from the electrochemical half cell are to be targeted to blood vessels beneath the skin, then a pattern of perforations could be cut into a pattern that mirrors the vascular system. As those blood vessels emerge at the surface, the ports for salt bridge can be wider, since their ions do not need to go as deep to reach a target. As those blood vessels go deeper within the body, the ports above them may be narrowed to provide a deeper penetration of ions to the target tissue.

The area of desired ion delivery can be changed not only by varying aperture, but also by varying spacing and patterning of ports for electrolyte exchange through the device. If the target is skin, then no particular control of salt bridge location or directionality of flow is required and the electrolyte can be in continuous contact with the skin with the active magnesium metal facing the person with an unimpeded path of ion flow to the skin.

Ionomers can be implemented to block one or all of the salt bridges in an electrolyte system. A positively charged polymer such as Polydiallyldimethylammonium chloride (polyDADMAC) will only allow negative ions to move. A negatively charged ionomer like nafion will only allow positive ions to move.

In addition, the type of ion allowed to move can also be selected by utilizing a size selective polymer that allows either one-way or two way flow. If a Two-way flow ionomer is desired for size selectivity, it can be stacked with a non-selective ionomer to enforce both flow of a particular charge of ion and a particular size of ion.

How-to Selection Guide for Salt Bridge Materials VS Desired Ion Transport

In more detail, the following characteristics of the salt bridge can be determined by the type of ion conducting polymer or gel utilized. Below is a simple selection guide for materials and methods for the salt bridge's most effective utilization for the user's end desired effects.

In some cases, salt bridge includes an ionomer, i.e. nafion. It allows movement of positive ions. Really small ions like H+ can go through, bigger ones could go along the surface (such as Mg++) of a rolled up tube. Negative ions cannot move along or through the membrane. This sets up an ionic "one way road". If a negatively charged ionomer such as nafion is used to make a salt bridge from an anode, this will no longer draw any negative ions out of an organism, but positive ions (the therapeutic agent) may be pushed in from the tip. With the use of an ionomer, the number of positive charges on drug molecules introduced into the body are equal to the number of negative charges on electrons.

If a salt bridge includes a neutral or zwitterionic gel and there is no charged ionomer, then negative ions can leave the organism and positive ions can enter the organism. There would be no way to know which predominates, and this could mean there is no consistent relationship between electron flow and ion flow.

Using an ionomer (one charge cannot move) allows accurate dosing. Comparably, iontophoresis may have inconsistent delivery of drug because there have to be other dissolved circulatory molecules.

2-Way Non-Selective Gel and Iontophoresis

With an anode, a salt bridge can push + into organism and pull − out.

With a cathode, a salt bridge can push + into organism and pull + out.

When the ion-conducting polymer is an ionomer type of charged ions that can flow is the opposite charge.

charged ionomer (nafion)

With an anode, a − salt bridge can push + ions into organism.
With a cathode, a − charged salt bridge can push + ions out of organism.

+ charged ionomer (polydiallyldimethylammonium chloride (polyDADMAC))

With an anode, a + charged salt bridge can pull − ions out of organism.

With a cathode, a + charged salt bridge can push − ions into organism.

Connection of a user to ground will have effects on the rate of flow and the direction of ion traffic after it leaves the salt bridge of the device. The effect will be like a crosswind and can be used to give directionality to ion and electron flow once these have travelled from the device to the organism. In one example, a ground wire in contact with the tip of the fingers draws ion and electron flow in a manner different from connecting it to a foot when the anode is connected to the leg. Likewise, grounding the foot ipsilateral to the device placement will have a different effect from ground placement contralateral to the device placement.

For cathode half-cells, precise contact with the target allows focusing of the resulting oxidative damage on the intended region of the target (e.g., a local infection or tumor) and limit damage of nearby structures (e.g., tissue). The extent and number of electrically conductive paths may be selected to guide electron flow through and around the intended region of the target. For example, if drug delivery is occurring simultaneously, the positioning of the electrically conductive path may influence whether the drug is driven into or away from the intended region of the target. In alternating use of anode and cathode half-cells, results may be improved if the anode half-cell is electrically coupled to the target at a time when the cathode half-cell is not electrically coupled to the target. This allows a more local effect and removes possibly unwanted effects of current flow on ion migration and cellular membrane integrity. For instance, if the target were a cancerous tumor, a cathode half-cell may be implemented at the intended region of the target for a length of time, followed by implementation of an anode half-cell at points distant from the intended region of the cathode half-cell target. In some cases, anode half-cells may be implemented to protect blood from generalizing the oxidation state of the tumor throughout the body. Blood may be treated on the return voyage through the vein with an anode half-cell to prevent the oxidation state induced from radiation or from a cathode half-cell from travelling and producing more general symptoms in the body.

Simultaneous use of cathode and anode half-cells may have a positive impact (killing undesirable cells) and a negative impact (killing desirable cells along the path between anode and cathode half-cell).

Figure 1D:
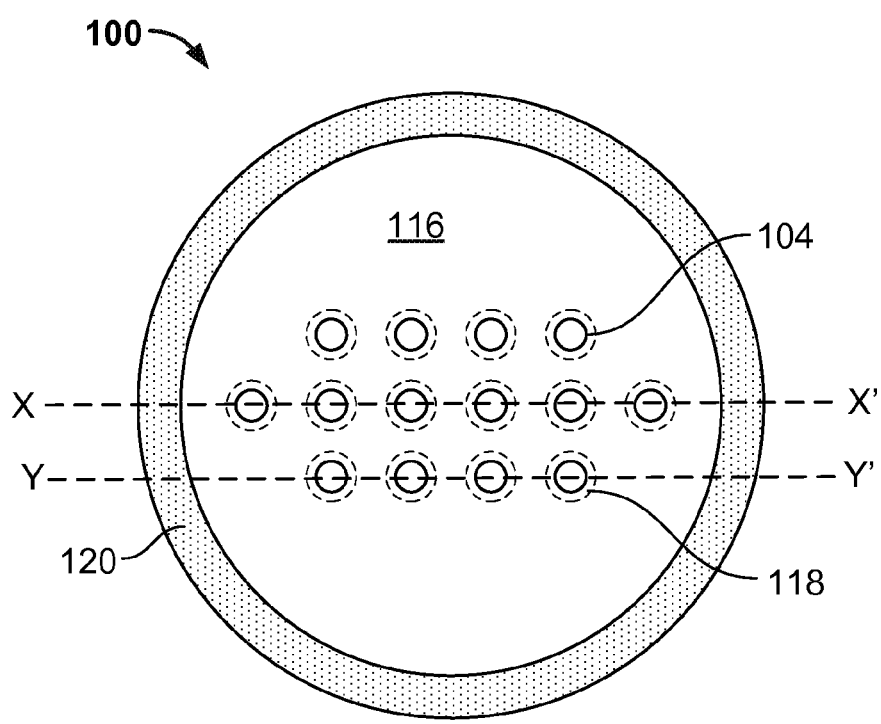

FIG. 1A depicts a cross-sectional view along XX' of FIG. 1D of an embodiment of a therapeutic electron transfer device 100 in the form of an adhesive patch. Therapeutic electron transfer device 100 includes half-cell 102. Half-cell 102 includes electrodes 104, active material 106, and electrolyte 108. Electrodes 104 are formed from an electrically conductive material, such as silver nitrate. Active material 106 may be, for example, magnesium. Active material 106 includes protrusions 110 and recessions 112. Electrodes 104 are formed on protrusions 110 of active material 106. Electrolyte 108 may be, for example, an electrolytic gel. Backing 114, together with electrically insulating layer 116, serves to at least partially contain electrolyte 108. Protrusions 110 and electrodes 104 extend through openings 118 in electrically insulating layer 116. Adhesive 120 allows therapeutic electron transfer device 100 to be adhered to a target. Backing 114 and electrically insulating layer 116 contain electrolyte 108, with ion flow between therapeutic electron transfer device 100 and the target occurring via openings 118.

When active material 106 is magnesium, electrodes 104 function as an anode. Electrodes 104 form an electrically conductive path between therapeutic electron transfer device 100 and the target, such that electrons flow to the target via electrodes 104. Ions (e.g., magnesium ions) flow from therapeutic electron transfer device 100 to target via openings 118 in electrically insulating layer 116 proximate electrodes 104. Openings 118 serve as a forced pathway for ions flowing between therapeutic electron transfer device 100 and the target, and thus form ionically conductive paths in the presence of an ionically conductive fluid or electrolyte.

An area of openings 118 may be increased to increase ion flow to the target or decreased to decrease ion flow to the target. When openings 118 are relatively small, electron and ion flow from therapeutic device 100 may be directed precisely and deeply to the target. Alternatively, when openings 118 are larger, the resulting increased level of ion flow over a larger contact area may cause ions to be driven more diffusely and less deeply into the target.

Electrically insulating therapeutic electron transfer device 100 in all but selected regions allows guided delivery of electrons or current to selected areas of the target while shielding other areas of the target. When ion flow is desired to be directed, a "bottleneck" may be created by reducing the area of openings 118 such that specific ions can be loaded and delivered to the target via electrolyte 108.

FIG. 1B depicts a cross-sectional view of an embodiment of therapeutic electron transfer device 130 similar to that of therapeutic electron transfer device 100, in which openings 148 have a diameter half that of openings 118 of therapeutic electron transfer device 100 shown in FIG. 1A. As such, ion flow from therapeutic electron transfer device 130 is directed more precisely and deeply than that of therapeutic electron transfer device 100.

Therapeutic electron transfer device 130 includes drug or nutritional supplement 132 proximate at least one of the one or more ionically conductive paths, such that the therapeutic device is configured to deliver the drug or nutritional supplement to the organism via the at least one of the one or more ionically conductive paths.

As depicted in FIGS. 1A and 1B therapeutic electron transfer devices 100 and 130 have an enclosure having a surface configured to contact the organism, and one or more ionically conductive paths are formed through the surface of the enclosure configured to contact the organism. In some cases, the flow rate of ions through the one or more ionically conductive paths at the surface of the enclosure is inversely related to the ratio of the total area of the one or more ionically conductive paths at the surface of the enclosure to the sum of the total area of the surface configured to contact the organism and the total area of the one or more ionically conductive paths at the surface of the enclosure.

Figure 1E:
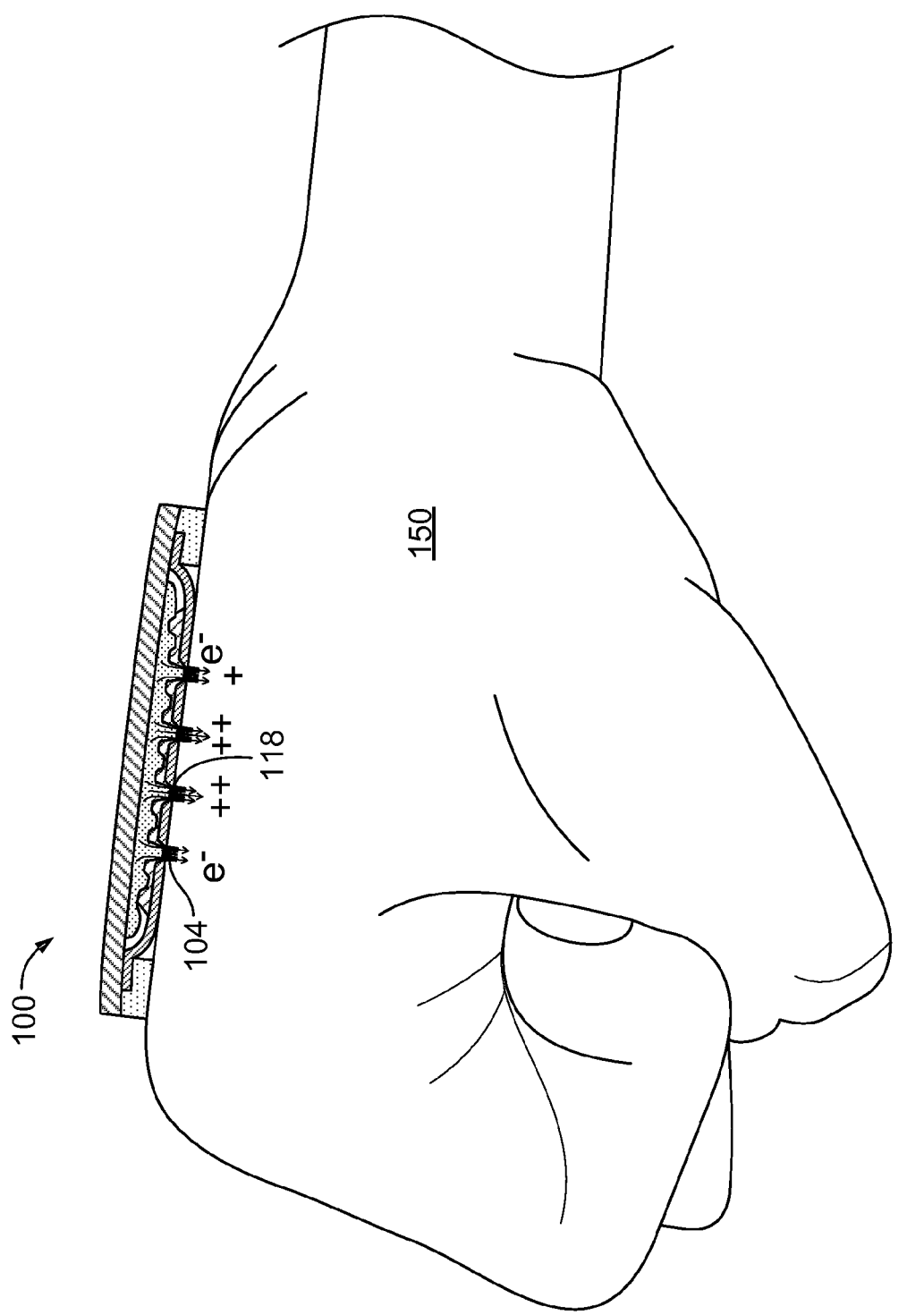
FIG. 1E depicts the therapeutic device of FIG. 1A coupled to a target.

FIG. 1C depicts a top view of therapeutic electron transfer device 100. FIG. 1D depicts a bottom view of therapeutic electron transfer device 100, with electrodes 104 protruding through openings 118 in electrically insulating layer 116. Adhesive 120 is positioned around a perimeter of therapeutic electron transfer device 100. FIG. 1E depicts a cross-sectional view along YY' of therapeutic device 100 of FIG. 1D electrically coupled to target 150 via electrodes 104 and ionically coupled to the target via openings 118. As depicted in FIG. 1E, target 150 is a hand.

One or more additives, such as catalysts, adsorbents, absorbents, and microbes, may be present (e.g., provided proximate the active material 106 or combined with the active material or electrolyte 108) in half-cell 102 to break down or adsorb unwanted reaction products or promote electron transfer to or from the target. In one example of an anode half-cell, manganese dioxide in the presence of a silver catalyst consumes gaseous hydrogen and hydrogen sulfide generated at an anode. In another example of an anode half-cell, activated carbon adsorbs hydrogen sulfide generated at an anode. In yet another example of an anode half-cell, populating the anode half-cell with acid-producing bacteria helps maintain activity of the anode. In one example of a cathode half-cell, manganese dioxide in the presence of a silver catalyst assists the breakdown of hydrogen peroxide, thereby accelerating withdrawal of electrons from the target by the cathode half-cell.

Implementations of half-cell 102 may include one or more additional features. As described herein, solids that dissolve during operation of a half-cell may be admixed with the active material to create pores in the active material. Surfaces of the active material may be exposed through structural disruption. Conductive materials such as carbon fibers may be combined with the active material to negate passivating surface corrosion by allowing passage of electrons from interior to exterior.

In some cases, two or more half-cells may be electrically coupled to a target for simultaneous or alternating use. In one example, two anode half-cells or two cathode half-cells are coupled to a target and used simultaneously to increase delivery or removal of electrons or treat different areas of a target. In another example, an anode half-cell and a cathode half-cell are applied to different areas of a target and are used alternately to achieve a desired effect.

Degradation of the active material may be observed by monitoring the appearance of the conductive material, the presence of odors such as that from hydrogen sulfide, changes in color, or loss of voltage as measured by a multimeter. For a cathode half-cell with hydrogen peroxide as an oxidizing agent, the presence of bubbles upon insertion of a test strip coated with manganese dioxide indicates effectiveness of the active material. An inactive half-cell may be replenished or replaced. In some cases, a passivating substance may be removed from a half-cell to restore activity. In one example, citric acid is used to expose a reactive surface. In another example, abrasion is used to expose a reactive surface.

Figure 2:
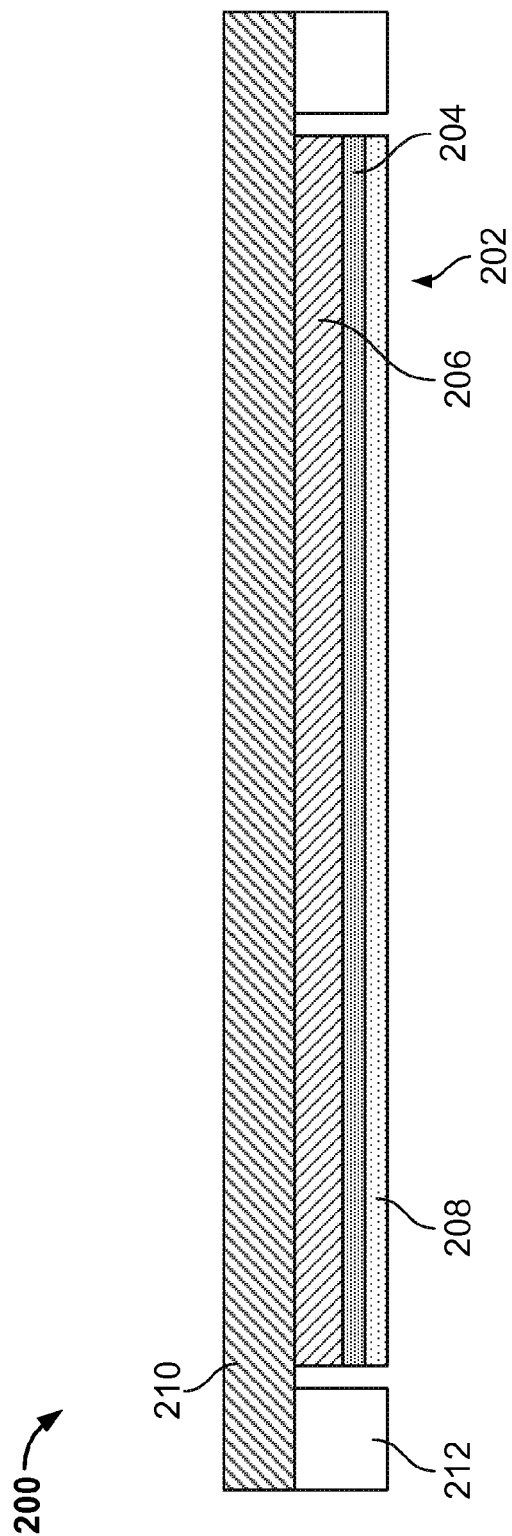
FIG. 2 is a cross-sectional view of another embodiment of a therapeutic electron transfer device in the form of an adhesive patch.

FIG. 2 depicts a cross-sectional view of an embodiment of a therapeutic electron transfer device 200 in the form of an adhesive patch. Electron transfer device 200 includes half-cell 202. Half-cell includes electrode 204, active material (for example, magnesium) 206, and electrolyte 208. Electrolyte 208 may be, for example, an electrolytic gel. Electrolytic gel 208 serves as an electrically conductive path between electrode 204 and a target, and also serves as an ionically conductive path between active material 206 and the target. Backing 210 at least partially contains electrolyte 208. Adhesive 212 allows therapeutic electron transfer device 200 to be coupled to a target. Eletctrolyte 208 provides an electrically and ionically conductive layer for transfer of electrons and ions between therapeutic electron transfer device 200 and the target. Thus, the flow of ions and electrons is more diffuse than that of therapeutic electron transfer devices 100 and 130 depicted in FIGS. 1A and 1B, respectively.

Figure 3:
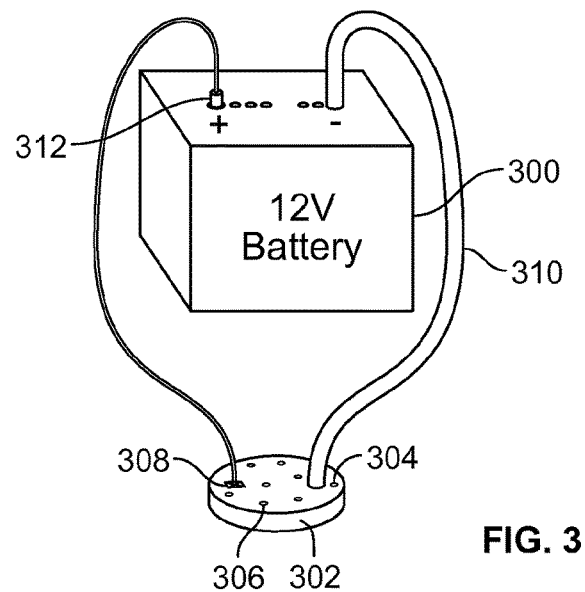
FIG. 3 depicts an embodiment of a therapeutic electron transfer device including a power source coupled to a target.

FIG. 3 depicts power source 300 coupled to target 302. As depicted, power source 300 is a 12 V battery, and target 302 is a Petri dish including electrolyte 304 upon which bacteria 306 has been grown. Target 302 is electrically coupled to power source 300 via electrode 308 and ionically coupled to the power source via salt bridge 310. Positive terminal 312 of power source 300 is electrically coupled to target 302 via electrode 308. Salt bridge 310 couples electrolyte 304 and the electrolyte solution of power source 300. As depicted, power source 300 is configured to induce oxidation of bacteria 306.

Figure 4:
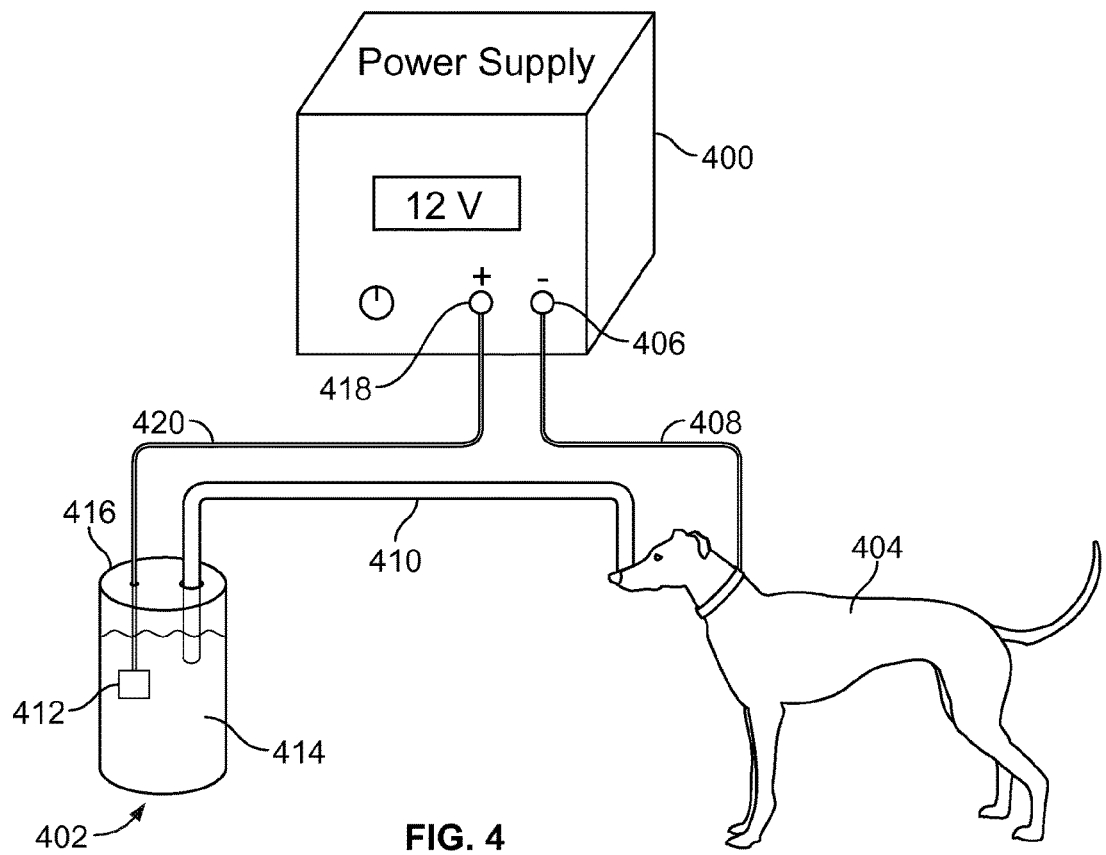
FIG. 4 depicts an embodiment of a therapeutic electron transfer device including a power source coupled to a target.

FIG. 4 depicts power source 400 and half-cell 402 coupled to target 404. As depicted, power source 400 is a 12 V battery, and target 404 is a mammal. Target 404 is electrically coupled to negative terminal 406 of power source 400 via electrical conductor 408 and ionically coupled to half-cell 402 via salt bridge 410. Half-cell 402 includes electrode 412 and electrolyte 414 in container 416. Electrolyte 414 includes an active material (e.g., bacterial cells, fungal pathogens, toxic biomolecules etc.) that is oxidized while power source 400 is electrically coupled to the electrolyte. Positive terminal 418 of the power source is coupled to electrode 412 via lead 420. As depicted, target 404 receives a net addition of electrons via lead 408.

Figure 5A:
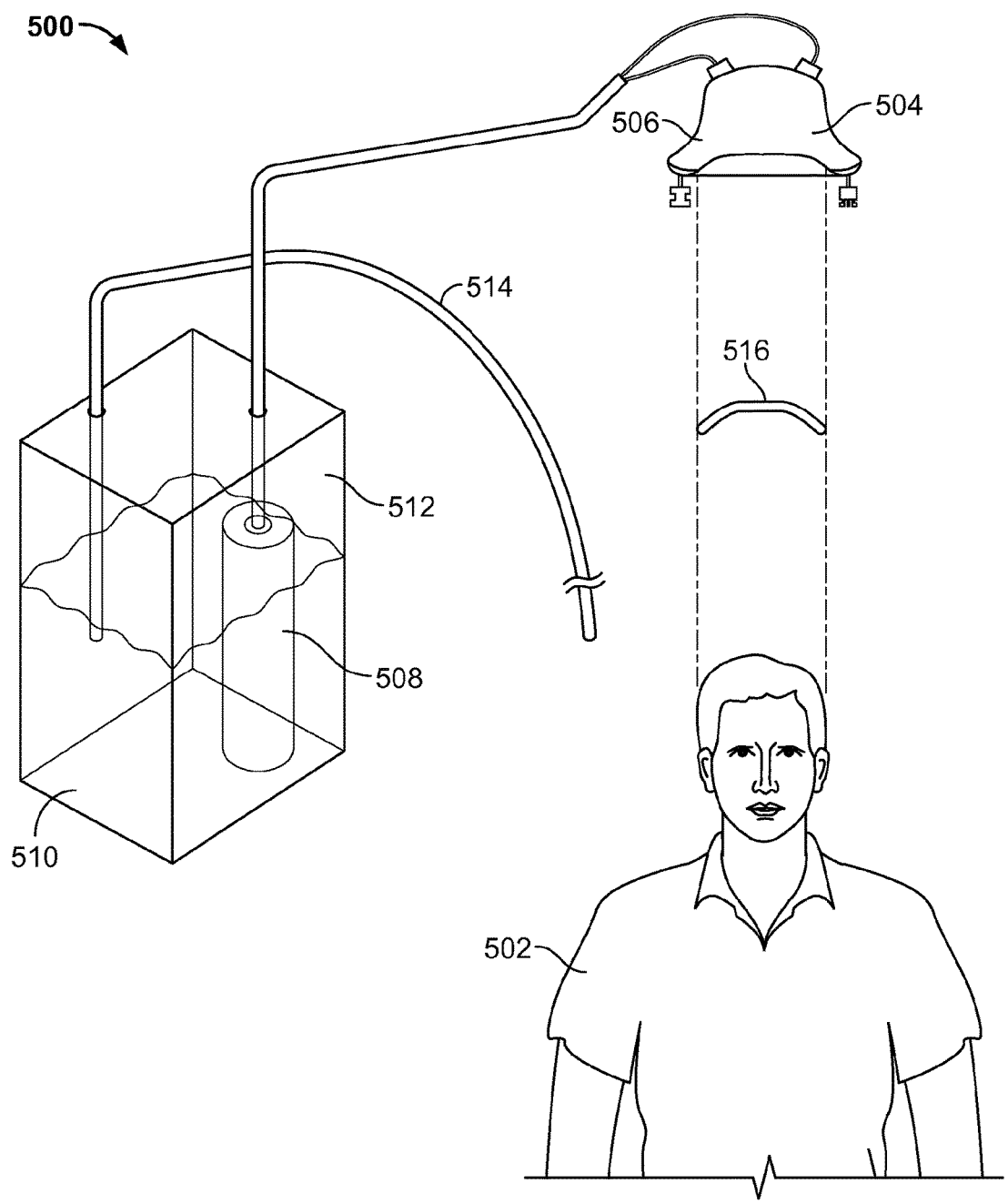
FIG. 5A depicts an exploded view of an embodiment of a therapeutic electron transfer device positioned proximate a target.

FIG. 5A depicts an exploded view of half-cell 500 electrically coupled to target 502 via structure 504. Structure 504 is configured to contact target 502 to achieve electron transfer between half-cell 500 and target 502. Half-cell 500 includes electrode 506, active material 508, and electrolyte 510 (e.g., 1M NaCl solution) in container 512. Electrode 506 is electrically coupled to structure 502. Salt bridge 514 is configured to form an ionically conductive path between half-cell 500 and target 504. In some cases, structure 502 is electrically coupled to target 504 via electrolytic gel 516.

Figure 5B:
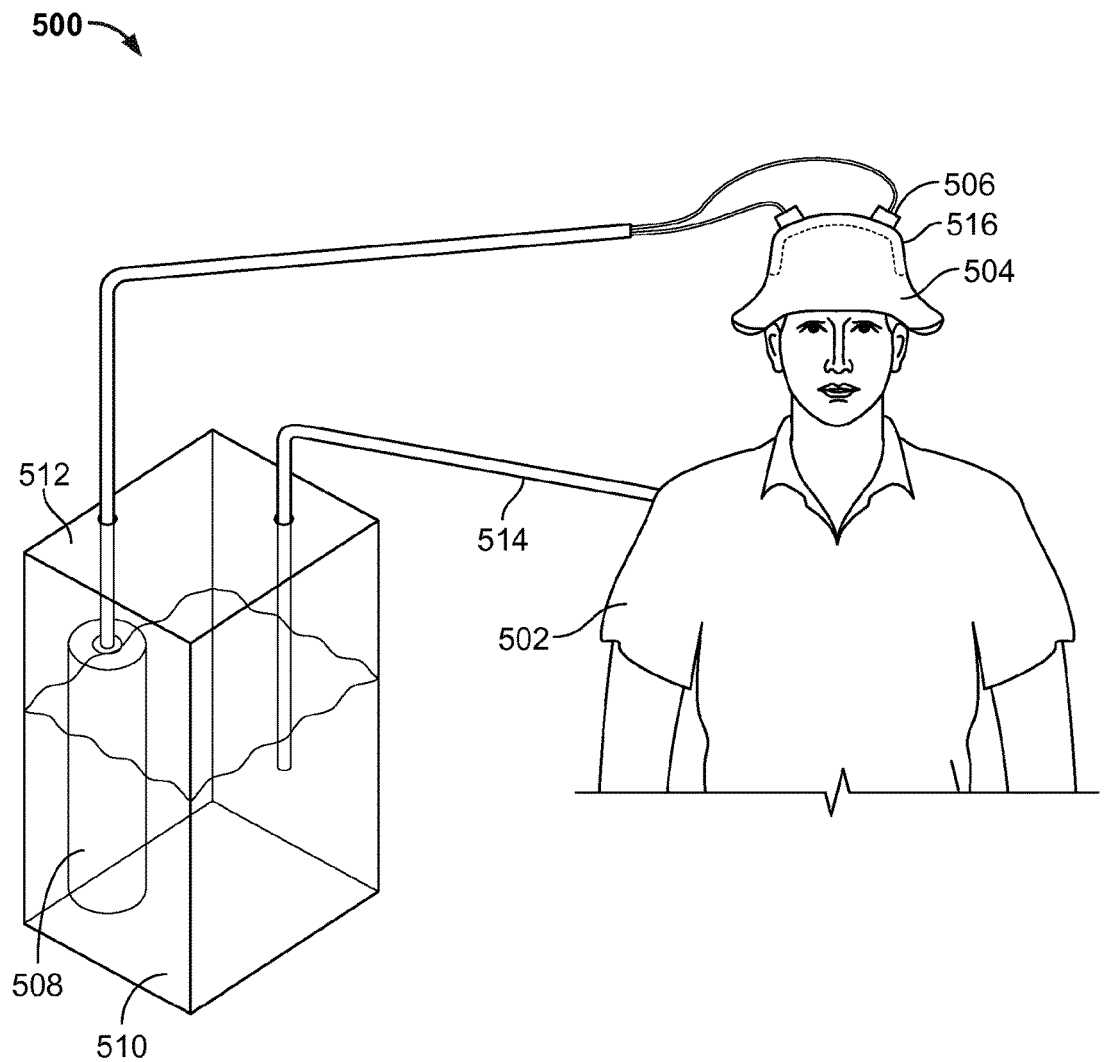
FIG. 5B depicts the therapeutic device of FIG. 5A coupled to the target.

FIG. 5B depicts half-cell 500 electrically coupled to target 502 via electrodes 506 coupled to structure 504 and ionically coupled to target 502 via salt bridge 514. Electrolytic gel 516 facilitates transfer of electrons between half-cell 500 and target 502. Ions flow between target 502 and half-cell 500 via salt bridge 514.

As depicted in FIGS. 5A and 5B, structure 504 is a helmet, and target 502 is a human. Structure 504 facilitates the flow of electrons between half-cell 500 and target 502. When half-cell 500 is an anode half-cell, electrons flow from the half-cell to target 502. When half-cell 500 is a cathode half-cell, electrons flow from target 502 to the half-cell. An active material made of magnesium or a power supply can provide the electrons needed for the system to function.

Figure 6:
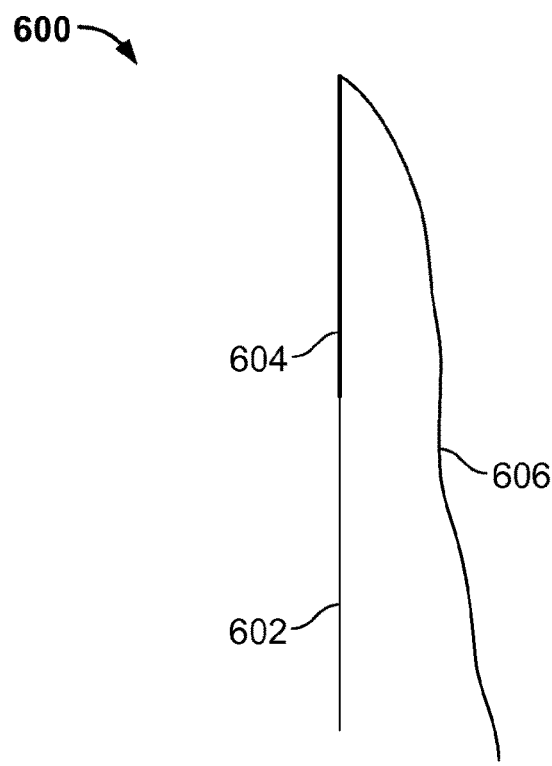
FIG. 6 depicts an embodiment of a therapeutic electron transfer device in the form of an acupuncture needle.

As depicted in FIG. 6, therapeutic device 600 is an acupuncture needle including electrical conductor 602, active material 604, and ionically conductive path 606 configured to be ionically coupled to the target. Electrical conductor 602 is a needle. Active material 604 is coated on one end of the needle. Ionically conductive path 606 may include, for example, an absorbent string soaked in electrolyte. Ionically conductive path 606 may be in contact with or wrapped around active material 604, thereby keeping the active material wet. When active material 604 is a reducing agent, such as magnesium or zinc, therapeutic device 600 functions as an anode half-cell, transferring electrons to the target via electrical conductor 602. Therapeutic device 600 allows electrons to be transferred to a target below the skin layer and deeper into the body. When active material 604 is an oxidizing agent, therapeutic device 600 functions as a cathode half-cell capable of removing electrons from and thus attacking an unwanted target such as an infection or growth.

In some implementations, one or more cathode half-cell needles ("oxidizing" needles) are inserted near an unwanted target and anode half-cell needles ("reducing" needles) are inserted in a perimeter around the oxidizing needles. The reducing needles act as a barrier, providing protection against the oxidizing effects spreading outward to the rest of the body. In certain implementations, rather than a coating with active material, electrical conductor 602 may be electrically coupled (e.g., via an electrically conductive wire) to a power supply, with the electrical conductor allowing the transfer of electrons to or from the target.

Figure 7:
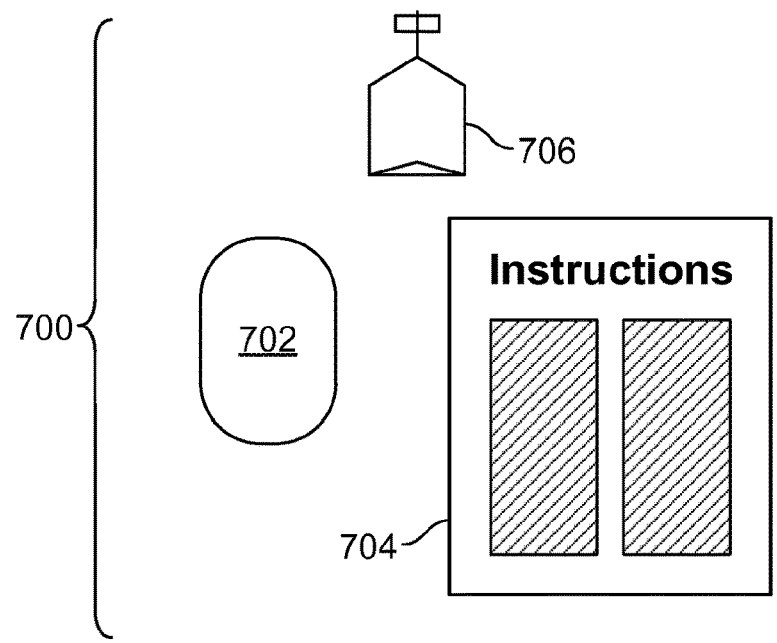
FIG. 7 depicts a kit including a therapeutic electron transfer device.

FIG. 7 depicts kit 700 including therapeutic electron transfer device 702 and instructions 704 for coupling the therapeutic electron transfer device to a target. Therapeutic electron transfer device 702 may be any embodiment of a therapeutic electron transfer device, such as those described herein. As depicted, therapeutic electron transfer device 702 is a top view of an adhesive patch such as those described in FIGS. 1A, 1B, and 2. Instructions 704 may include instructions for replacing or maintaining therapeutic electron transfer device 702. In some cases, therapeutic electron transfer device 702 includes an electrolyte. In certain cases, electrolyte 706 or an electrolyte precursor is included with kit 700, and instructions 704 include instructions for preparing the electrolyte, delivering the electrolyte to therapeutic electron transfer device 702, or both.

Examples of formulation, shape, and methods of manufacturing anode half-cells are described in more detail below.

Magnesium may be solidified on a conductive material by solidifying molten magnesium about a conductive support. In one example, wire is wound into a spiral shape and fit into a toroidal mold. Two or more strands of the wire cross through the middle of the hole of the torus for later use as a clip and point of electrical contact. The mold is closed and molten magnesium is poured into the cavity, where it coats the wire and the external surface of the mold. Before the magnesium has time to cool completely, the molten magnesium is decanted from the mold to leave behind a hollow interior chamber shaped by the path of the wires, not covered with a coat of magnesium.

The melting point of magnesium is 1,202° F. (650° C.) while the melting point of copper is 1,984° F. (1,085° C.). If a silver-coated anode wire is used, then the temperature of the magnesium should be brought up to 1,763° F. (961.8° C.) to sinter the magnesium and silver. Molten magnesium can be brought up to a temperature close to the melting point of the wire metal and then poured across the wire frame structure. Magnesium vaporizes at 1090° C., so cannot be heated above this point without boiling. The wire may be coated with magnesium by using the electrolytic method from molten magnesium chloride ($MgCl_2$). The magnesium may also be deposited as a vapor onto the wire by a method similar to distillation. This may be accomplished during the production of the magnesium using the Pidgeon process to avoid the energy costs of re-melting magnesium.

The hollow interior chamber forms a cavity. This cavity can be injected with a water-based fluid containing potassium sulfate or some other soluble salt compatible with human skin and preferably non-toxic. An electrolytic gel may help prevent spillage in an open half-cell. A flowing thin electrolyte may also be employed and may be benefit from agitation due to movement.

In one example, the wire has a spiral shape that allows fluid to flow through and past the magnesium. Hydrogen bubbles may agitate fluid at the magnesium surface and promote the movement of fluid surrounding the magnesium.

An electrolyte may be introduced into the anode half-cell and mixed to promote activity at the anode surface in one or a combination of ways, some of which are described below.

In one example, a salt is mixed with water or other fluid prior to activation of the half-cell. This is a practical option for injection of the electrolyte, where the half-cell is a dry half-cell activated with addition of electrolyte. These dry half-cells may be multiple electrolyte use devices, in which a single anode half-cell has several portions of fresh electrolyte pushed through it (e.g., through separate channels).

In another example, an anode half-cell includes dry (salt) components, and water is added to the half-cell to dissolve the salt, thereby forming the electrolyte in the half-cell as needed. A half-cell may contain an electrolyte precursor, and water may be added to the cell to form an electrolyte. The slow dissolution of salts and wicking of electrolyte may help extend the period over which the anode will be active and make the activity more consistent. For instance, if salt crystals are precipitated onto the conductive material prior to magnesium casting, then the water touching the surface of the salt on the anode interior will dissolve a channel deeper in the surface of the active material. This provides a fresh surface of active material and may create a more consistent effect over time.

In yet another example, dry (salt) and wet components are pre-filled in an anode half-cell and separated by a barrier. Puncture of the barrier allows the dry and wet components to mix, thereby forming the electrolyte in situ. Separating salts from a gel help prevent premature activation of the half-cell. Upon rupture of the barrier between them, the half-cell becomes active.

In yet another example, the half-cell contains fluid in contact with the active material, and all components needed for the half-cell are present, but a component must be admixed with the fluid in the half-cell to initiate activation of the half-cell.

In yet another example, all components needed for the half-cell to function are pre-mixed and included in the half-cell, but during manufacturing the magnesium is passivated to inhibit its activity. The half-cell may be activated by mixing some material into the anode such as citric acid that removes the barrier coating on the surface and allows reactions to proceed.

Once the salts meeting electrolyte activate the surface of the magnesium a series of chemical reactions occur that result in the formation of magnesium ions:

$$Mg(s) \rightarrow 2e^- + Mg^{2+}$$

Magnesium can also react directly with steam to make hydrogen gas and magnesium hydroxide:

$$Mg(s) + 2H_2O(g) \rightarrow Mg(OH)_2(aq) + H_2(g)$$

Magnesium can also react with acid in the solution to make hydrogen. This reaction does not contribute electrons to the organism, instead, the acid $H^+$ is the electron acceptor and hydrogen gas is emitted. In the equation below, citric acid is used in the example, but any acid with a soluble counterion can be utilized. Citric acid is utilized in this example because of its low hazard, solid form, and high solubility when chelating magnesium ions.

$$Mg(s) + H_3C_6H_5O_7(aq) + \rightarrow Mg^{2+}(aq) + HC_6H_5O_7^{2-}(aq) + H_2(g)$$

Additionally, chelating agents can be added to the electrolyte to increase magnesium ion solubility. This may prevent the unproductive interaction of magnesium ions and hydroxide or carbonate, which form insoluble precipitants on the surface of the anode.

Even after the precipitants build up, there may be more rapid erosion of the anode in areas where a precipitant is not built up. This will lead to consumption of the anode by undermining. Building the anode so it sheds fouling precipitants in each domain may help maintain the consistency of the reactions. If the half-cell is reoriented or agitated, function may be improved.

A path for ion flow and removal of $Mg^{2+}$ buildup of ions may be achieved in one or a combination of ways, some of which are described below.

In one example, magnesium is allowed to migrate out of the half-cell to the target. If sulfates or chlorides are present in the electrolyte, the magnesium will move readily as soluble $Mg^{2+}$. This may cause crowding of ions with elemental Mg as the solid source and positively charged $Mg^{2+}$ ions being created and moving away from the anode. These magnesium ions migrate in the direction of current flow (opposite the flow of electrons). The result is iontophoresis of magnesium ions at the target. Magnesium salts have outstanding safety when applied topically, and topical applications of magnesium chloride and magnesium sulfate are considered to be safe and have been used for direct application of moist salts to the surface of the skin and wounds. No particular pain or reaction is noted, and most users experience relaxation and easing of muscle tension. Contact of magnesium ions at very high concentrations with skin (saturation) has no apparent negative result. If direct absorption of magnesium is acceptable, then this $Mg^{2+}$ can be the ion that travels down the salt bridge and into the target to balance charges. This migration of $Mg^{2+}$ will inhibit a buildup of magnesium ions in the solution that would otherwise inhibit further reactions. Negative ions will be drawn toward the site of attachment toward the anode. A salt paste may be applied to the anode to provide a reservoir of negative ions to migrate away from the target into the anode.

In another example, magnesium ions are allowed to build up in the electrolyte, and then fresh electrolyte is added and old electrolyte discarded to renew the anode function of the half-cell until all or substantially all of the elemental magnesium is converted to ions. This will lead to a decrease in anode performance as magnesium builds up in the electrolyte and an immediate increase in performance when electrolyte is renewed.

Designs for anodes may inhibit large internal bubbles and allow hydrogen gas bubbles upward flow to participate in the anode face "scrubbing". Convection type flow in a large excess of electrolyte can promote effective functioning of a small anode. In some cases, the active material may have a hollow or clamshell shape that allows fluid to flow through the active material and acts as a reactive surface. In addition, refinements to surface geometry promote more even activity of the anode throughout operation. In one example, the active material has sufficient strength to hold itself together, but not enough strength to hold up a layer of Mg(OH)$_2$ and MgCO$_3$. A formulation with these erosive characteristics promotes self-cleaning by the anode. Surface geometry and internal spaces will determine how and when the anode comes into activity. Addition of water can be slowed down by putting dissolvable plugs in internal chambers of the active material, with dissolution of a plug leading to a new fresh network of magnesium to start reacting and dissolving with. Dissolving plugs may be formed of low-solubility salts, and therefore may also electrolyte conductivity.

Hydrogen is made when magnesium reacts with water, splitting it and turning it into hydrogen gas (H$_2$) and magnesium hydroxide Mg(OH)$_2$; This reaction does not yield electrons that can be delivered via a conductive path to the target. The electrons lost by magnesium are given to hydrogen gas.

Hydrogen production at the anode surface agitates the electrolyte flow around the anode as the bubbles escape. This gives a hydrogen producing anode a more vigorous, refreshing electrolyte flow. The production of hydrogen also creates insoluble magnesium hydroxide, which may foul the surface of the anode which limits the anode rate of reaction.

Hydrogen generated by a half-cell may be removed in one or a combination of ways, some of which are described below.

In one example, a hydrogen fuel cell may be used to harness evolved hydrogen. In another example, hydrogen may be disposed of via failsafe venting. No matter how much acid is present in the electrolyte, the magnesium anode is expected to contribute electrons directly to the user via the conductive path. The hydrogen and its utilization in a fuel cell becomes an interesting "side effect" of using an element as active as magnesium. If zinc were used as the sacrificial anode, there would be almost no splitting of water and no production of hydrogen until the temperature reaches boiling.

In another example, hydrogen is removed via reaction with MnO$_2$:

$$MnO_2 + \tfrac{1}{2}H_2 \rightarrow MnO(OH) + e-$$

This reaction can be reversed by exposure to oxygen in the air, and may allow renewal by drying of the anode half-cell and allowing atmospheric air to circulate.

In some cases, generated hydrogen is not utilized, but rather vented into the environment or oxidized to water using a catalyst at the opening of the vent. For disposable half-cells, venting is a suitable option. If hydrogen were to build up in a half-cell, there could be a failsafe deformation of the cell to accommodate the increasing volume of gas inside. This may be achieved via a pop-up button, a sliding apart of the anodes, or a hydrogen-permeable membrane.

If a hydrogen-permeable membrane were permeable to oxygen and carbon dioxide, these could provide valuable reactants to the system. A membrane in the shape of a tube may be inserted into the anode electrolyte cavity. At one end, deep inside the cavity, the tube may be closed off. At the surface of the anode it is clipped in place by the lid of the anode. The length and amount of surface area needed for the membrane to be effective at making the system "breathe" can be determined experimentally. The collapsed tube of membrane preferably has a gap with a spacer inside to allow free circulation of air, but take up little space needed for electrolyte. The electrolyte side of the membrane can be seeded with magnesium carbonate crystals to make the precipitation trap.

To facilitate efficient function, an anode has surfaces where the active material (e.g., magnesium or other material that serves as the anode) ions can migrate. If a magnesium surface is dry, the buildup of magnesium ions quickly inhibits the oxidation reaction. If there is only a small amount of surface area, the anode may not be able to produce much current. In some cases, a spiral structure within the anode that offers a long contiguous channel may be used. The metal may be hot poured, vapor deposited, or electroplated onto a labyrinthine scaffold. The interior of the anode is contacted with an electrolyte solution to increase the surface area for reactions and ion migration. With cathodes, increased surface area inhibits bottlenecks in the quantity of electrons that can be withdrawn.

When a cathode half-cell is electrically coupled to a target, the target functions as an anode half-cell, and electrons are transferred from the target to the cathode half-cell. This configuration is suitable for therapeutic applications such as cancer treatment. While coupling an anode half-cell to the area of the tumor may mitigate the toxic effects of radiation, a cathode half-cell may be synergistic with radiation therapy and help to destroy the stressed cells introducing additional stress. A cathode half-cell may be implemented by placing an half-cell patch or half-cell electrically coupled to a piercing over a cancerous area which would pull electrons from the area during treatment to promote oxidative damage and mutation of cancerous cells, killing them. This would have the advantage of being a targeted effect, with less and less impact of electron withdrawal as the distance from the treatment site increases. The choice of cathodic substance with less potent effect (less voltage) may be used to reduce the collateral damage of electron withdrawal. As the difference in voltage between the target and the oxidizing agent increases, the distance at which tissues will have electrons withdrawn increases as well. Weaker oxidizing agents will exert their impact over a shorter range than more powerful ones.

Cathode half-cells may also be implemented with power sources and can function as a local medical tool targeted to the problems caused by invading organisms or cancers. Accuracy and potency can be achieved by using electrically insulated conductors and implanted probes to withdraw electrons at one location with the effect diminishing in a spherical pattern and also with passage through resistive materials.

A cathode half-cell may have a construction similar to that of anode half-cells described herein. Given the more corrosive environment of the cathode half-cell, different material choices may be advantageous. Suitable conductive materials include carbon fiber fabric and platinum wire. A conductive material added to plastic may be used to create a watertight, non-corrodible barrier with the appropriate electrical conductivity. One example of a suitable active material is hydrogen peroxide. Hydrogen peroxide is a stable oxidizing agent and can be recharged or replaced to maintain activity. It is safe to dispose of and is not irrevocably damaging if rinsed quickly after being spilled on skin. The conductive path is connected to the hydrogen peroxide and is secured to the user to induce oxidative stress in tissues.

In summary, the carbon fiber cable contacts the target. The electrically non-conductive watertight enclosure is the plastic case. The oxidizing agent is hydrogen peroxide. The conductive scaffold is carbon fiber. The user is able to transport the half-cell with them as they move about. This half-cell does not direct current through the body, but withdraws electrons from the body.

Electrode surface fouling can be mitigated by using a properly formulated electrolyte and alloys of an element such as magnesium that are designed to shed its oxidized coating. An electrode may be designed with a textured surface to provide enhanced surface area for reaction and increase effect. Texturing of the conductive material that makes electrical contact with the target may also increase the surface area for electron transfer into the user. Imperceptible texturing or etching of the surface can improve electron transfer many-fold and can provide a surface that electrolyte pastes or gels cling to readily when compared to a smoother surface.

A cathode half-cell for cancer treatment has advantages of providing specific targeted treatment that is localized compared to ingested chemotherapy/antibiotics. Some therapies such as radiation have a degree of targeting, but because the beam goes straight through the body, many unintended tissues are damaged. Also, the radiation is a potent direct oxidizer, so many times the damage of radiation cannot be completely reversed by antioxidant action; i.e. if DNA in a normal cell is hit by a gamma ray, there may be damage that cannot be repaired or reversed. In contrast, a cathode would act electrically to create a general deficit of electrons. A cathode half-cell allows selective application of the radical inducing effects to the intended region of the target.

A cathode half-cell may promote release ions from corroding medicinal particles such as colloidal silver. Colloidal silver nanoparticles can be delivered to a site of infection and allowed to absorb into the tissues while near an anode half-cell. Once silver has penetrated throughout the infected area, it can be "activated" using a cathode half-cell to make it corrode very quickly, delivering the ionic silver needed to disrupt infections. The nanoparticles diffuse differently when they are neutral (not corroding). The flow of electrons into the body from an anode may exert an iontophoretic "push" of the silver nanoparticles into tissues. Once there, switching to a cathode may corrode the silver nanoparticles, releasing silver ions ($Ag^+$) at the desired site. This use of the anode and cathode half-cells in alternation allows rapid delivery of nanoparticles such as silver with rapid activation and immobilization that would inhibit off-target effects.

Figure 8A:
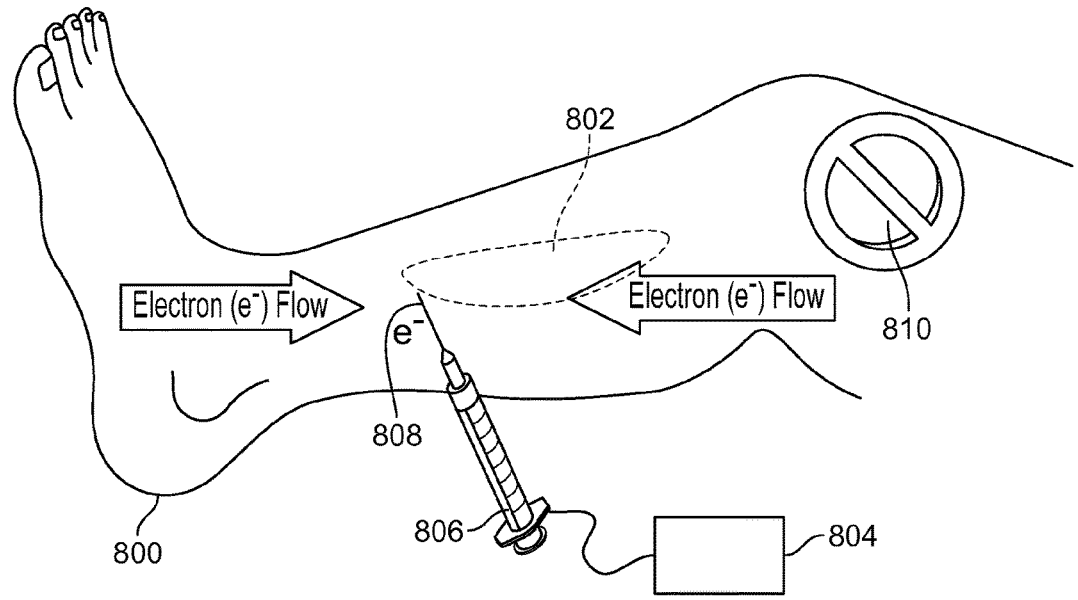
FIGS. 8A and 8B depict alternating use of two therapeutic electron transfer devices coupled to a target.

Anode and cathode half-cells have opposite effects. Alternating anode and cathode half-cells on the target may be used to reduce damage caused by cathodes during therapeutic treatment. FIG. 8A depicts target 800, a human leg having cancerous tumor 802. Cathode half-cell 804, which may be a half-cell including hydrogen peroxide as an oxidizing agent or a power source, is coupled to syringe 806, with conductive needle tip 808 serving as an electrode from the cathode half-cell to the tumor 802. Instead of a straight cone of damage caused by radiation, tip 808 in contact with tumor 802 creates a rough sphere of oxidative damage from the point of the conductive tip outward. The spherical nature may be perturbed by materials of different electrical conductivity within the sphere of influence, but for the most part, the effect will be a sphere with branches that reach more distantly into blood vessels because of their high electrical conductivity. There is a pause in the motion of blood during the cycle of the heartbeat. In some cases, cathode half-cell 804 is activated when the blood is motionless, withdrawing electrons from tumor 802. Cathode half-cell 804 may then be deactivated when the blood is moving. When the blood is motionless, anode half-cell 810 is inactive.

Figure 8B:
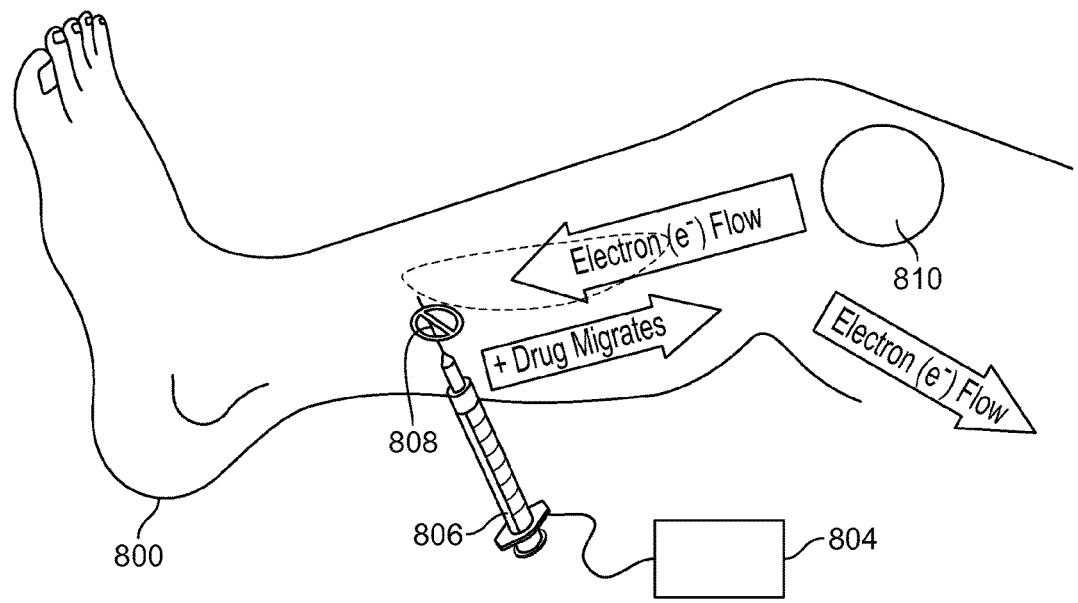

As depicted in FIG. 8B, when the blood is in motion, anode half-cell 810 is activated (e.g., electrically coupled to the target via an intravenous needle), thereby providing electrons to the blood to mitigate the negative impact of electron withdrawal by the cathode on the blood. In this example of a tumor in the leg, the blood is oxidized while it is motionless in the foot, but as it travels back from the leg, it encounters the electron donating effect of the anode, which reverses many of the deleterious effects of oxidation and inhibits the blood from spreading the free radical chain reactions induced by the cathode in the leg. Such sparing effects may be practiced with other technology such radiation, with radiation applied at the time when blood is still, and an anode being applied directly to the bloodstream while blood is in motion. Radiation is more difficult to direct than a cathode half-cell, and typically has a wider swath of damage, while a cathode is a spherical phenomenon selectively directed to the intended region of the target.

Alternation of anode and cathode can also be used for surface or pool sanitation, since the alternation from an electron surplus to an electron deficiency rapidly and frequently would tend to kill microbes adhering to a surface.

EXAMPLES

Example 1: Oral Anode Half-Cell

A chewable anode half-cell provides a quick release of electrons to an oral target. Formation of the chewable anode half-cell includes selecting a gum base and combining the gum base with a conductive substance to yield a conductive material. Suitable gum bases include chicle and 1,3-butadiene. Activated carbon is a selected as a biocompatible, chewable conductive substance. Magnesium particles are combined with the conductive material as the active material. In some cases, the activated carbon is incorporated into the magnesium particles during formation, thereby reducing the insulation of magnesium by formation of insulating magnesium hydroxide during use. The lack of toxicity and nutritive value of magnesium ions makes elemental magnesium a suitable option for oral applications of anode half-cells. Calcium may be added to enhance nutritional value and reduce the laxative effects of the magnesium. Solids or salts selected to dissolve during use may be added to impart flavor, electrolytic properties, enhance release of electrons, or a combination thereof. A coating, such as a candy coating, may be provided on the exterior of the anode half-cell to insulate the half-cell and inhibit discharge of electrons before use.

During use, saliva functions as an electrolyte for the chewable anode half-cell. The electrolyte bathes the chewable anode half-cell and is replenished by secretion and swallowing. Chewing provides disruption and breaks up the solid particles of magnesium, thereby reducing the impact of magnesium hydroxide passivation by refreshing surfaces of the particles and exposing new surfaces. Electrons are released quickly, at a rate that can be accelerated or slowed by the chewing energetics, and gaseous hydrogen and hydrogen sulfide are liberated. Gaseous hydrogen may be released via the mouth or ingested. The activated carbon adsorbs some of the hydrogen sulfide, minimizing the associated odor.

Electron transfer to the target is enhanced by locating the anode half-cell inside the mouth. The conductive activated carbon allows electrons to travel from the magnesium particles to the surface of the anode half-cell, and then into the target. The conductive path to the target is through the saliva and other electrolytes present in the chewable anode half-cell. Contact with the teeth and gums provides a moist, oil-free path into the target.

Example 2: Oral Cathode Half-Cell

An oral cathode half-cell effectively withdraws electrons from an oral target. The cathode half-cell is prepared by combining hydrogen peroxide and an electrolyte solution in an enclosure, such as a pouch. A conductive material is placed in the enclosure, such that the oxidizing agent/electrolyte solution contacts the conductive material. Silver wire (e.g. in the form of a scaffold) is selected as the conductive material. Silver has excellent electrical conductivity and yields antimicrobial silver ions. A catalyst such as manganese dioxide may be placed in the enclosure to catalyze the decomposition of hydrogen peroxide. In some cases, such as when a short range effect, low voltage, low activity, or a combination thereof is desired, the catalyst is omitted. Agitation or disruption is not needed for operation of the cathode half-cell, at least because the electrolyte and the oxidizing agent are mixed.

The cathode half-cell is placed proximate an area in the mouth to be treated, such as an infected tooth. The silver support and the electrolyte may function as a conductive material to transport electrons from the target to the cathode. In some cases, a conductive wire or foil may be used to conductively couple the silver support with the area to be treated. The cathode half-cell may be placed in a mouthpiece such that the area to be treated is electrically coupled to the cathode half-cell while other areas of the target are shielded from the electron-withdrawing properties of the cathode half-cell. Electron flow from the area to be treated may be enhanced by applying a conductive paste to the mouthpiece such that the conductive paste contacts the area to be treated. A non-conductive paste may be applied to other areas of the mouthpiece. A mouthpiece can be used for overnight treatment to allow a long duration treatment with a relatively low potency rather than an intense, short-duration treatment that may impair normal tissue surrounding the area to be treated. In some cases, conductive material such as salts or activated carbon may be added to a non-conductive paste to yield a conductive paste.

Example 3: Alternation of Oral Anode Half-Cell and Oral Cathode Half-Cell

In some cases, use of an oral anode half-cell and an oral cathode half-cell, such as those described in Examples 1 and 2, respectively, may be alternated. In one example, an oral anode half-cell is used during the day and an oral cathode half-cell is used at night. The oral anode half-cell may be implemented on a side of the mouth opposite of that treated by the oral cathode half-cell. Alternating use of the oral anode half-cell and oral cathode half-cell allows the oral anode to mitigate effects of the oral cathode half-cell on teeth and other tissue surrounding the treatment area.

Example 4: Cathode Half-Cell Near a Site of Infection or Tumor

A cathode half-cell electrically coupled to a target near a site of infection or tumor is activated when the blood has paused in the rest phase of the pumping action of the heart. When blood is moving, the cathode half-cell is switched off and an anode half-cell is activated "downstream" over the venous blood flow. To further protect the blood from cathodic effects, the cathode half-cell may be implanted in tissues that have only capillaries, not near major arteries and veins. The anode half-cell, in contrast, is placed near or into a major artery or vein to increase the distribution and efficacy of the anodic effect. In some cases, a magnet may be placed over an artery or vein to make even an externally applied anode more effectively applied to the blood.

Example 5: Active Materials Internally Implemented

An active material, such as magnesium, can be inserted into a target. This can put the site of action closer to the desired location in the target. An anode may be formulated and attached to the desired site of action via a shielded wire, which may be exposed at the tip, for instance. This may allow a targeted effect for cathodes, where the target of the effect may be in a very small area. Anodes may be implemented similarly by insertion into body cavities followed by removal when the anode is depleted. A therapy for inflammatory disease of the bowels, for instance, may be designed using a magnesium anode with a conductive outer surface that allows electron transmission into the target tissue. In Crohn's disease, the use of an anode that is swallowed and passes through the digestive tract may reduce the inflammation response that depletes many of the body's circulating antioxidants.

Example 6: Magnesium Anodes with Revealed Metallic Scaffolds

In an indicator function, the conductive support may become apparent when the magnesium anode has dissolved. To use this, the anode may have a transparent viewing window or just bare magnesium on the visible surface. As the magnesium inside the anode degrades, it begins to reveal the differently colored and uncorroded scaffold beneath. Suitable scaffold materials for magnesium include copper, gold, and carbon fiber, which are differently colored from the magnesium. Silver and all of the other silvery metallic substances would be less advantageous for the indicator function in pairing with magnesium, but may have some particular texture or pattern etched into their surfaces to make it apparent to users that this is not just the magnesium surface any more. Likewise, the scaffold may be patterned in such a way as to make it apparent to the user when revealed. An example includes a scaffold shaped with text such as "renew anode" or "replace anode."

One implementation is to use a mesh of twisted copper wire with a plated silver filigree pattern on the wire surface. This wire is twisted into a reticulate shape to create a 3D labyrinth and placed in a mold. Magnesium may be vapor-deposited or plated by electrolysis onto the wire surface, or molten magnesium may be poured into the mold and excess is poured out before it all hardens to leave an inner cavity for electrolyte. The copper wires with their silver streaks surface where the anode clips onto the conductive lead the user holds. This point of contact promotes electrical contact throughout the anode. The cavity left after the magnesium is poured out is injected with electrolyte solution to exclude air and capped.

One example is an electrochemically active earring back. When the seal is pierced and the earring post goes in, ethanol bathes the lobe followed by electrically conductive gel. The magnesium begins to degrade. As the magnesium ions are liberated into the electrolyte solution, the copper scaffold may be revealed. When the magnesium has oxidized to ions, the electrolyte wire and gel may be discarded or recharged by recoating magnesium on the copper and silver scaffold. Depleted half-cells may be restored, disposed of, or used in an inactive state.

Example 7: Flowing Electrolyte

User activity may be used to pump electrolyte from a clean reservoir of gel, through an active material and then to a Mg²⁺ saturated gel "waste" side. This waste electrolyte may be disposed of in a garden as plant nutrient or continuously excreted by the device as an electrolyte paste to help maintain electrical contact with the skin.

Example 8: Revealing Anode Age Using a Mirrored Surface

An amulet may be fashioned similar to the earring back above, but with the magnesium (or other anode substance) filling the transparent side of the necklace. The electrical contact is via the chain the amulet hangs from and may also be accomplished via the metal of the amulet. In this case, there is no piercing of the electrolyte, though a small compressible dispenser nipple and inlet may keep the electrolyte cycling through the amulet on a regular basis. This would inhibit the self-inhibitory buildup of magnesium ions in the electrolyte, allowing a much higher quantity of magnesium to electrolyte in the initial package. This gel may be formulated with some colloidal silver and ethyl alcohol as a preservative; it may also act as a hand sanitizer.

One example of a gel formulation includes carrageenan as a base and is suitable for lotion, lubricant, or ingestible. This sort of device may be much larger and contain a larger charge of magnesium, but with regular changes of the electrolytic gel it eventually dissolves and the mirrored surface starts to turn gray at the edge like an old, corroded silver mirror. The user is not looking for the scaffold to be revealed in this case, but rather a clouding of the mirror-like surface where the silvery magnesium is degrading. This may use a metallic silvery colored wire, but may be bolstered by a differently colored metal.

Example 9: Attachment Via Piercing

Piercings may have some anodic properties, but these are small, and advances in metallurgy have made piercings that have almost no corrosion. An half-cell may be coupled to the body via a piercing.

Example 10: Anodic Protection for Tubs and Pools

Baths, pools and spas may be electrically coupled to an anode half-cell. In some implementations, a honeycombed magnesium structure may be introduced into the water.

Example 11: Impressed Cathodic Protection Via Power Source

A pool or spa electrically coupled to a cathode half-cell may be switched on when a bather enters the pool and switched off after leaving. Cathode half-cell function may be achieved by power source. In a therapeutic setting, voltage may be adjusted according to the aggressiveness of treatment and the client's tolerance for the effects.

Example 12: Impressed Positive Charge for Withdrawal of Electrons

Withdrawal of electrons via a power source may help enhance the effectiveness of other treatments that generate free radicals to kill cancer or invading organisms. This could also be used to corrode silver particles when colloidal silver is used for wound disinfection. Impressing a positive charge would make the silver nanoparticles in the wound corrode vigorously, releasing positive ions of silver and driving them through the tissue. This effect may be enhanced by applying a current across the tissue in one direction (ions driven right) and then the leads flipped (ions driven left), thoroughly saturating all tissues inside a wound with a technique called iontophoresis. Silver ions are very effective at killing microbes and sparing human tissue. Withdrawal of electrons may cause damage to cancer cells and infectious microbes without needing to be paired with other treatments.

Example 13: Social/Sensual Use of Electrical Currents

Anode half-cells may be used to create impressed currents for social/sexual stimulation. In one example, if partners are exchanging body fluids and a first partner has magnesium anode earrings on, the current flows from the earrings through the first partner and into the second partner via the electrolyte connection between them. In another example, an anode half-cell may be electrically coupled to an electrically conductive condom. Other examples include switching charge and alternating the current flow through partners via a power source controller.

Example 14: Therapeutic Person to Person Contact

When a therapist stands on an anodic mat or wears anodic earrings, they may act as a conduit for the charge, directing it to the most useful locations. These effects can be enhanced by allowing the patient to act as a path for electrons instead of simply being a dead end. While charge flow is not new matter, it is useful for practitioners to understand and utilize charge flow diagrams for certain treatments. An anode or cathode half-cell may be used to induce charge flow, especially when used as an anode and cathode pair connected at different points on the body (i.e., a battery). An anode (electron donating device) may be attached without also attaching an external cathode. This makes the organism the cathode for the system. Likewise, a cathode may be attached without also attaching a corresponding anode.

Example 15: Therapeutic Use of Anodes in Psychotherapy and EMDR Therapy

Eye Movement Desensitization and Reprocessing (EMDR) therapy makes use of sensations or movements that alternate left to right during a subject's recounting of their traumatic events. This allows a more complete processing of the information between hemispheres and has had remarkable success especially among those with Post Traumatic Stress Disorder (PTSD). A person who connects to ground at the waist or feet and holds two electrodes in his hands may be subject to left side then right side charge flow. Given the ability to switch the grounding of the left foot and the right foot in alternation or harmony with the anodic charge coming through the hands may offer therapists an unobtrusive method of EMDR alternating lateral stimulation. When the technology first was conceived, the alternation was with eye movement; the initials still grace the EM in EMDR is from Eye Movement. Since that time, vibrating probes have been used held in the person's hands. These were much less distracting and worked better than a clumsy follow the original eye movement in a metronome-like fashion.

The effects of an electrically coupled anode half-cell may be applied in any setting. With EMDR, the difference is that alternating the laterality of the anode may enhance the effect of the alternating lateral stimulation already a part of EMDR therapy.

Example 16: Alternation of Anode and Cathode for Conductive Surface Sanitation Alternating a surface or body of fluid from an anodic to a cathodic system may diminish the viability of microorganisms. If this alternation is undertaken rapidly, the ability of microbes to adapt to the change may be diminished. The greater the amplitude of the voltage change, the more deleterious the effect will be and the more rapidly the process will sterilize. This may be applied to floors, counters, cookware, pools, etc. These surfaces may be maintained in a negatively charged state when users are present to provide the positive health benefits of electrons, and will only alternate to cathodic when users are not present to touch the surfaces.

Example 17: Use of Anodes in Implants

Using an anode half-cell or other source of electrons delivered on, in, or near the site of a medical device implant can greatly slow or stop its corrosion. For a magnesium and zinc implant, the action of a magnesium anode may cathodically protect the zinc in the implant. The implant may remain un-degraded while the magnesium anode is attached. Half-cells may be used to stage corrosion at a rate that complements bone ingrowth to the implant.

Implants may be formulated with a scaffold of magnesium alloy that is slow to degrade and a filler material of pure magnesium that is designed to degrade fairly rapidly and in an uncontrolled manner. Because the filler magnesium is not structurally significant, it may be used as a "time delay" sacrificial anode directly and intimately coupled to the more critical Mg—Zn alloy (other alloys are possible). This would allow users to not wear an external anode until this pure Mg filler material is corroded. At that time, the doctor could examine the rate of bone ingrowth and might prescribe an externally worn sacrificial anode if the bone has not yet woven itself through the mesh structure of the load bearing Mg—Zn alloy.

Example 18: Use of Externally Applied Anodes to Prevent Degradation of Metal Implants Metal implants are designed to take the role of a joint when the joint has worn out or has broken catastrophically. The metals are susceptible to oxidation. Corrosion makes the load bearing surfaces rough, impairing joint function and further scraping material from the metal surface leading to a positive feedback cycle where more wear means more corrosion. In some cases, oxidation may be halted by adding an external anode or power source to donate electrons near the site of the implant.

Example 19: Use of Anodes after Traumatic Injury

Many types of traumatic injury are immediately followed by an oxidative cascade, where cells spill their oxidizing agents and lead to a chain reaction of cell death.

Example 20: Post Injury Prevention of the Oxidative/Excitotoxic Cascade

On the battlefield or in many sports, one of the most common injuries is Traumatic Brain Injury (TBI). Application of an anode half-cell to the head of a TBI victim may diminish the chain-reaction death that comes from oxidative pollution by dead cells within the brain. Electrons can neutralize these released toxic oxidizers before they have a chance to kill neighboring cells that were undamaged by the initial traumatic incident. Because cathodes can be applied immediately to even an unconscious patient, this allows a quicker response time than intravenous injection. In cases where blood flow is interrupted, like stroke, an anode half-cell may be beneficial.

Example 21: Use of Anode Half-Cells to Inhibit Oxidation of Food During Cooking If an electrically conductive pan were connected via wire to a source of electrons, the corrosion of the pan and the oxidation of the food may slow or halt, even though the temperature increases and the water activity goes up. This may allow products to be protected from the damage of oxidation that usually occurs during cooking, and may inhibit the contamination by metal ions that typically catalyze oxidation after cooking.

Example 22: Use of Anode Half-Cells on Freshly Slaughtered Animals or Newly Harvested Produce When an animal is killed or a fruit is picked, a series of death signals are transmitted through the flesh. Many of the oxidizing agents held at bay in cellular compartments get released, and the resulting oxidation of tissues reduces nutritional quality and flavor. With some products like red meat, there is an additional fermentation step needed to make the product flavorful, tender, and digestible. While the action of microbes and their enzymes are desirable, oxidation competes with longer fermentations. Anode half-cells can be connected to meat before the fermentation process to inhibit oxidation. Anode half-cells may also be connected to produce after harvesting, thereby reducing losses to oxidation during shipping and improving nutritional quality.

Example 23: Use of Anodes to Inhibit Metal Corrosion in Canned Goods

Applying an anode to the exterior of canned goods during production, shipping, and retailing may reduce oxidation of the metal and eliminate the need for interior plastic coating. An anode half-cell mounted to the exterior of the can may resolve issues of pressurization and provide an externally visible indication of product safety. In some cases, anode half-cells may be electrically coupled to an interior of canned items.

Example 24: Mortuary Use

Anode half-cells and anode-cathode half-cell alternation may be implemented to protect the bodies of the dead from degradation. Half-cells provide a non-invasive way to preserve the dead until embalming, and may supplant the antioxidants used in the embalming process.

Example 25: Ionic Drug Delivery

A device can be tailored to deliver ions of a therapeutic nature to the organism. These ions may be drugs or they may be minerals and vitamins that are nourishing. Some nutrients, like magnesium ions also have drug-like effects when they occur in a tissue concentration which is higher than usual. If targeting the skin surface with the ions, then electrolyte contact can be maximized. The delivery of the ions is usually targeted to some tissue beneath the epidermis, and the perforations on this device as shown in FIG. 1A would drive the ions in the hole deeply into tissues because of the narrow aperture of the salt bridge between the organism and the half-cell. Magnesium ions are well known to relieve muscle spasms. The skin is only a barrier to the delivery of magnesium ions to the muscle and the blood. The absolute number of ions delivered is less important than the depth to which they are delivered. Larger opening than those shown in FIG. 1A would provide penetration that is broader and less focused and would be appropriate to treat a skin condition rather than a muscular condition.

This device can be further tailored to deliver its electrons and ions to specific tissues beneath the surface of the skin. A pattern of perforations in the device can determine how much and how deeply the ions loaded into the perforations ports can travel. If targeting blood vessels, for instance, there may be areas of shallow blood vessels and areas where these vessels travel deeper beneath the skin. Narrow apertures are favored to target deeper tissues, while larger apertures can be utilized for shallow tissue penetration.

The device is further optimized if the electrochemistry of magnesium occurs in an area separate from the point of ion transfer into the organism. The salt bridge acts to transfer ions at some distance away from the anode or cathode materials. This allows the electrolyte at the interface of the organism to be composed of substantially different chemistry than would be ideal for the corrosion of the anode. This distance allows the end of the salt bridge to be specialized, such as loading valuable drug compounds into the end of the salt bridge where the electrolyte has contact with the organism. The drug may be loaded within an acidic gel, and at some point after the drug has entered the body, the acidic condition changes to basic because of the action of magnesium, which turns acid ($H^+$) into hydrogen gas. This may allow a pH gradient in the elution of the drug and promote maximum delivery, efficiency and efficacy.

The device can be optimized further through the use of a grounded connection connected to the organism at the same time as an anodic or cathodic ion delivery device. This is expected to influence the direction of ion flow such that drugs could be made to flow around bones or provide directionality other than simply orthogonal to the patch, which is expected without the addition of a ground.

Example 26: Integration with Clothing

Either through the use of thin sheets or foil inserts put into pouches on clothing or the use of conductive fibers in clothing connected to an anode, a user can get the protection body wide or wherever the conductive threading is. This may be useful for astronauts or commercial airline pilots who are exposed to higher levels of radiation from the sun and outer space. The reducing technology can help minimize the side effects or even prevent the free radicals from forming and damaging DNA and cells.

The device can be modified to deliver or remove a specific type of ion charge (+ or −) via the use of an ionomer in a solid or gelled matrix. This ionomer will impede the flow of same charged ions and allow flow of only one type of ion (− or + respectively). An example of this could be shown with the negatively charged ionomer nafion, which allows only positive ions to move across its surface or through. In the case of lateral flow of ions, size is not a selection criteria, and in the case of ions flowing through the membrane, both size and charge are factors for the type of transfer. A nafion tube filled with water, closed at the end and ionically connected through the middle would be expected to accumulate H+ ions, the only ions small enough to travel through the membrane. If two sheets of membrane are sandwiched and used as an ionically conductive path, then ions of any size can transfer along the face of the membrane. Conversely, the same set of possibilities exist with a positively charged polymer such as Polydiallyldimethylammonium chloride (polyDADMAC) will only allow negative ions to move. Transfer of ions across the face of the ionomer will not be size selective, but the ionomer can have innate blocking properties based upon size or it can be hybridized in a two layer system to a second material that restricts the size of the ions that can move down the ionic connection.

This "one way ion flow" is expected to increase the rate and velocity of ion flow for the selected ion which flows through the ionically conductive path compared to a non-selective "two way flow". Increasing rate and velocity of the ions as they reach the organism has implications for the depth of delivery and the speed of the drug/nutritional component's action.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A therapeutic device comprising:
a half-cell comprising:
an electrically conductive electrode;
an active material in contact with the electrode, the active material comprising an oxidizing agent or a reducing agent; and
one or more electrically conductive paths for electron transfer between an organism and the electrode, and
one or more ionically conductive paths for ion transfer between the organism and the half-cell,
wherein the half-cell, when electrically coupled to the organism, functions as a first half-cell of a galvanic cell and the organism functions as a second half-cell of the galvanic cell, wherein the half-cell comprises an additive in contact with the active material, wherein the additive increases the rate of electron transfer between the half-cell and the organism.

2. The therapeutic device of claim 1, wherein the half-cell comprises an electrolyte in contact with the active material.

3. The therapeutic device of claim 2, wherein the half-cell comprises a container configured to contain the electrolyte, the electrode, or both.

4. The therapeutic device of claim 1, wherein the active material comprises an oxidizing agent, and the therapeutic device, when electrically coupled to the organism via at least one of the one or more electrically conductive paths, withdraws electrons from the organism via the at least one of the one or more electrically conductive paths.

5. The therapeutic device of claim 1, wherein the active material comprises a reducing agent, and the therapeutic device, when electrically coupled to the organism via at least one of the one or more electrically conductive paths, transfers electrons to the organism via the least one of the one or more electrically conductive paths.

6. The therapeutic device of claim 1, wherein the electrode comprises the active material.

7. The therapeutic device of claim 1, comprising a single half-cell.

8. The therapeutic device of claim 1, wherein the therapeutic device forms a galvanic cell when electrically and ionically coupled to the organism.

9. The therapeutic device of claim 1, comprising a support configured to position the therapeutic device proximate the organism or to couple the therapeutic device to the organism.

10. The therapeutic device of claim 1, wherein at least one of the one or more ionically conductive paths comprises a salt bridge configured to allow ion transfer between the organism and the half-cell.

11. The therapeutic device of claim 1, wherein the therapeutic device is configured to achieve a net transfer of electrons to or from the organism.

12. The therapeutic device of claim 1, comprising a drug or nutritional supplement proximate at least one of the one or more ionically conductive paths, wherein therapeutic device is configured to deliver the drug or nutritional supplement to the organism via the at least one of the one or more ionically conductive paths.

13. The therapeutic device of claim 1, wherein the therapeutic device places an ionomer with a single charge (+ or −) immobilized in a solid or gelled matrix impeding the flow of same charged ions and allowing flow of only one type of ion (− or + respectively).

14. The therapeutic device of claim 1, wherein the additive is activated carbon.

15. The therapeutic device of claim 1, wherein the additive is acid-producing bacteria.

16. The therapeutic device of claim 1, wherein the additive is manganese dioxide in a presence of a silver catalyst.

17. A therapeutic device comprising:
a half-cell comprising:
an electrically conductive electrode;
an active material in contact with the electrode, the active material comprising an oxidizing agent or a reducing agent; and
one or more electrically conductive paths for electron transfer between an organism and the electrode, and
one or more ionically conductive paths for ion transfer between the organism and the half-cell,
wherein the half-cell, when electrically coupled to the organism, functions as a first half-cell of a galvanic cell and the organism functions as a second half-cell of the galvanic cell, wherein the half-cell comprises an additive combined with the active material, wherein the additive increases the rate of electron transfer between the half-cell and the organism.

18. The therapeutic device of claim 17, wherein the additive is activated carbon.

19. The therapeutic device of claim 17, wherein the additive is acid-producing bacteria.

20. The therapeutic device of claim 17, wherein the additive is manganese dioxide in a presence of a silver catalyst.

* * * * *